US012649715B2

(12) United States Patent
Jacobson

(10) Patent No.: US 12,649,715 B2
(45) Date of Patent: Jun. 9, 2026

(54) INHIBITORS OF NOROVIRUS AND CORONAVIRUS REPLICATION

(71) Applicant: COCRYSTAL PHARMA, INC., Bothell, WA (US)

(72) Inventor: Irina C. Jacobson, Sammamish, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 636 days.

(21) Appl. No.: 17/917,959

(22) PCT Filed: Mar. 17, 2021

(86) PCT No.: PCT/US2021/022657
§ 371 (c)(1),
(2) Date: Oct. 10, 2022

(87) PCT Pub. No.: WO2021/206877
PCT Pub. Date: Oct. 14, 2021

(65) Prior Publication Data

US 2023/0131564 A1 Apr. 27, 2023

Related U.S. Application Data

(60) Provisional application No. 63/008,195, filed on Apr. 10, 2020.

(51) Int. Cl.

| | |
|---|---|
| ***C07D 207/267*** | (2006.01) |
| ***A61P 31/14*** | (2006.01) |
| ***C07D 401/12*** | (2006.01) |

(52) U.S. Cl.
CPC .......... *C07D 207/267* (2013.01); *A61P 31/14* (2018.01); *C07D 401/12* (2013.01)

(58) Field of Classification Search
CPC ... C07D 207/267; C07D 401/12; A61P 31/14; A61K 31/4015
See application file for complete search history.

(56) References Cited

U.S. PATENT DOCUMENTS

| | | | |
|---|---|---|---|
| 4,079,038 | A | 3/1978 | Choi et al. |
| 4,093,709 | A | 6/1978 | Choi et al. |
| 4,131,648 | A | 12/1978 | Choi et al. |
| 4,138,344 | A | 2/1979 | Choi et al. |
| 4,180,646 | A | 12/1979 | Choi et al. |
| 4,304,767 | A | 12/1981 | Heller et al. |
| 4,353,656 | A | 10/1982 | Sohl et al. |
| 4,501,729 | A | 2/1985 | Boucher et al. |
| 4,778,054 | A | 10/1988 | Newell et al. |
| 4,811,731 | A | 3/1989 | Newell et al. |
| 4,946,931 | A | 8/1990 | Heller et al. |
| 5,035,237 | A | 7/1991 | Newell et al. |
| 5,590,645 | A | 1/1997 | Davies et al. |
| 5,860,419 | A | 1/1999 | Davies et al. |
| 5,873,360 | A | 2/1999 | Davies et al. |
| 5,968,543 | A | 10/1999 | Heller et al. |
| 6,413,536 | B1 | 7/2002 | Gibson et al. |
| 6,596,296 | B1 | 7/2003 | Nelson et al. |
| 6,613,355 | B2 | 9/2003 | Ng et al. |
| 6,632,666 | B2 | 10/2003 | Baust et al. |
| 6,667,371 | B2 | 12/2003 | Ng et al. |
| 6,732,732 | B2 | 5/2004 | Edwards et al. |
| 6,749,835 | B1 | 6/2004 | Lipp et al. |
| 6,766,799 | B2 | 7/2004 | Edwards et al. |
| 6,848,197 | B2 | 2/2005 | Chen et al. |
| 6,956,021 | B1 | 10/2005 | Edwards et al. |
| 7,008,644 | B2 | 3/2006 | Batycky et al. |
| 7,032,593 | B2 | 4/2006 | Johnston et al. |
| 7,048,908 | B2 | 5/2006 | Basu et al. |
| 7,146,978 | B2 | 12/2006 | Edwards et al. |
| 7,182,961 | B2 | 2/2007 | Batycky et al. |
| 7,252,840 | B1 | 8/2007 | Batycky et al. |
| 7,279,182 | B2 | 10/2007 | Lipp et al. |
| 7,384,649 | B2 | 6/2008 | Batycky et al. |
| 7,678,364 | B2 | 3/2010 | Edwards et al. |
| 2009/0105279 | A1 | 4/2009 | Cannizzaro et al. |

(Continued)

FOREIGN PATENT DOCUMENTS

| | | | |
|---|---|---|---|
| EP | 69715 | A1 | 1/1983 |
| GB | 2064336 | A | 6/1981 |

(Continued)

OTHER PUBLICATIONS

"Structure-Guided Design and Optimization of Dipeptidyl Inhibitors of Norovirus 3CL Protease. Structure-Activity Relationships and Biochemical, X-ray Crystallographic, Cell-Based, and In Vivo Studies" ACG Kankanamalage, Y Kim, PM Weerawarna et al. Journal of Medicinal Chemistry 2015 58 (7), 3144-3155 (Year: 2015).*
"Synthesis of tripeptide-type SARS-CoV 3CLpro inhibitors with a highly electrophilic carbonyl group" D Sarma, Diganta, T Regnier, K Hidaka, S Konno, U Bacha, E Freire, Y Kiso, Y Hayashi Peptide Science (2010), 46th, 311-314 (Year: 2010).*
"C1'-Cycloalkyl Side Chain Pharmacophore in Tetrahydrocannabinols" DP Papahatjis, VR Nahmias, SP Nikas, T Andreou, SO Alapafuja, A Tsotinis, J Guo, P Fan, and A Makriyannis J Med Chem, vol. 50, pp. 4048-4060 (Year: 2007).*
"Two- and Three-dimensional Rings in Drugs" M Aldeghi, S Malhotra, DL Selwood, AWE Chan Chem Biol Drug Des, vol. 83, Issue 4, pp. 450-461 (Year: 2013).*
Appleyard et al., A plaque assay for the study of influenza virus inhibitors, J. Antimicrob. Chemother., 1(4 Suppl):49-53 (Dec. 1975).
Berge et al., Pharmaceutical Salts, J. Pharm. Sci., 66(1): 1-19 (Jan. 1977).

(Continued)

*Primary Examiner* — Kara R. Mcmillian
*Assistant Examiner* — Sophia P Hirakis
(74) *Attorney, Agent, or Firm* — MARSHALL, GERSTEIN & BORUN LLP

(57) ABSTRACT

Methods of inhibiting the replication of noroviruses and coronaviruses in a biological sample or patient, of reducing the amount of noroviruses or coronaviruses in a biological sample or patient, and of treating norovirus and coronavirus in a patient, comprising administering to said biological sample or patient a safe and effective amount of a compound of Table A, or a pharmaceutically acceptable salt thereof.

2 Claims, No Drawings

(56) References Cited

U.S. PATENT DOCUMENTS

| | | | |
|---|---|---|---|
| 2014/0243341 | A1 | 8/2014 | Chang et al. |
| 2019/0345101 | A1 | 11/2019 | Cameretti et al. |
| 2022/0112177 | A1 | 4/2022 | Liu et al. |

FOREIGN PATENT DOCUMENTS

| | | | |
|---|---|---|---|
| GB | 2129691 | A | 5/1984 |
| GB | 2169265 | A | 7/1986 |
| GB | 2178965 | A | 2/1987 |
| GB | 2242134 | A | 9/1991 |
| WO | WO-97/43305 | A1 | 11/1997 |
| WO | WO-99/31122 | A1 | 6/1999 |
| WO | WO-03/15798 | A1 | 2/2003 |
| WO | WO-2005/023335 | A2 | 3/2005 |
| WO | WO-2005/095400 | A1 | 10/2005 |
| WO | WO-2006/061714 | A2 | 6/2006 |
| WO | WO-2007/084557 | A2 | 7/2007 |
| WO | WO-2010/148197 | A1 | 12/2010 |
| WO | WO-2013/049382 | A2 | 4/2013 |
| WO | WO-2013/138236 | A1 | 9/2013 |
| WO | WO-2015/073481 | A1 | 5/2015 |
| WO | WO-2016/037953 | A1 | 3/2016 |
| WO | WO-2016/045598 | A1 | 3/2016 |
| WO | WO-2017/13364 | A1 | 1/2017 |
| WO | WO-2017/097234 | A1 | 6/2017 |
| WO | WO-2017/133667 | A1 | 8/2017 |
| WO | WO-2017/198122 | A1 | 11/2017 |
| WO | WO-2017/222935 | A1 | 12/2017 |
| WO | WO-2018/042343 | A2 | 3/2018 |
| WO | WO-2020/030143 | A1 | 2/2020 |

OTHER PUBLICATIONS

Chou et al., Quantitative analysis of dose-effect relationships: the combined effects of multiple drugs or enzyme inhibitors, Adv. Enzyme Regul., 22:27-55 (1984).

Dragovich et al., Structure-based design, synthesis, and biological evaluation of irreversible human rhinovirus 3C protease inhibitors. 2. Peptide structure-activity studies, J. Med. Chem., 41(15):2819-34 (Jul. 1998).

Furuta et al., T-705 (favipiravir) and related compounds: Novel broad-spectrum inhibitors of RNA viral infections, Antiviral Res., 82:95-102 (2009).

Galasiti Kankanamalage et al., Structure-guided design and optimization of dipeptidyl inhibitors of norovirus 3CL protease. Structure-activity relationships and biochemical, X-ray crystallographic, cell-based, and in vivo studies, J. Med. Chem., 58(7):3144-55 (Apr. 2015).

Holford et al., Understanding the dose-effect relationship: clinical application of pharmacokinetic-pharmacodynamic models, Clin. Pharmacokinet., 6(6):429-53 (Nov.-Dec. 1981).

International Application No. PCT/US2018/028986, International Search Report and Written Opinion, mailed Jul. 13, 2018.

International Application No. PCT/US2021/022656, International Search Report and Written Opinion, mailed Sep. 16, 2021.

International Application No. PCT/US2021/022657, International Search Report and Written Opinion, mailed Sep. 17, 2021.

International Application No. PCT/US2021/022680, International Search Report and Written Opinion, mailed Aug. 9, 2021.

Kim et al., Reversal of the Progression of Fatal Coronavirus Infection in Cats by a Broad-Spectrum Coronavirus Protease Inhibitor, PLoS Pathog., 12(3):e1005531 (Mar. 2016).

Kim et al., Reversal of the progression of fatal coronavirus infection in cats by a broad-spectrum coronavirus protease inhibitor, PLOS Pathogens, 12(3):e1005531 (Mar. 2016).

Mandadapu et al., Inhibition of norovirus 3CL protease by bisulfite adducts of transition state inhibitors, Bioorg. Med. Chem. Lett., 2391):62-5 (Jan. 2013).

Muratore et al., Small molecule inhibitors of influenza A and B viruses that act by disrupting subunit interactions of the viral polymerase, Proc. Natl. Acad. Sci. USA, 109(16):6247-52 (Apr. 2012).

Perera et al., Protease inhibitors broadly effective against feline, ferret and mink coronaviruses, Antiviral Res., 160:79-86 (Dec. 2018).

Shigeta et al., Synergistic anti-influenza virus A (H1N1) activities of PM-523 (polyoxometalate) and ribavirin in vitro and in vivo, Antimicrob. Agents Chemother., 41(7):1423-7 (Jul. 1997).

Thanigaimalai et al., Design, synthesis, and biological evaluation of novel dipeptide-type SARS-CoV 3CL protease inhibitors: structure-activity relationship study, Eur. J. Med. Chem., 65:436-47 (Jul. 2013).

Willis et al., Therapeutic liposomal dry powder inhalation aerosols for targeted lung delivery, Lung, 190(3):251-62 (Jun. 2012).

Yang et al., Synthesis, crystal structure, structure-activity relationships, and antiviral activity of a potent SARS coronavirus 3CL protease inhibitor, J. Med. Chem., 49(16):4971-80 (Aug. 2006).

Zhang et al., α-Ketoamides as Broad-Spectrum Inhibitors of Coronavirus and Enterovirus Replication: Structure-Based Design, Synthesis, and Activity Assessment, J. Med. Chem., 63(9):4562-78 (May 2020).

* cited by examiner

INHIBITORS OF NOROVIRUS AND CORONAVIRUS REPLICATION

FIELD OF THE DISCLOSURE

This disclosure relates generally to inhibitors of norovirus and coronavirus replication, and methods of treating or preventing norovirus and coronavirus infections by administering the inhibitors to a patient in need of treatment thereof.

BACKGROUND

Noroviruses are important enteric pathogens involved in non-bacterial gastroenteritis outbreaks worldwide. Noroviruses mainly occur from person to person via the fecal-oral route but also through contaminated food or water. Indirect contamination is also possible owing to the persistence of the virus in the environment. Human noroviruses belong to the genus Norovirus, family Caliciviridae and are non-enveloped viruses with a positive-sense, single-stranded RNA genome. Norovirus strains are classified into seven groups. Viruses belonging to groups GI, GII, and GIV infect humans, while groups GII, GIII, GIV, GV, GVI and GVII NoVs have been described in animals.

Coronaviruses are a family of common viruses that cause a range of illnesses in humans from the common cold to severe acute respiratory syndrome (SARS). Coronaviruses can also cause a number of diseases in animals. Coronaviruses are enveloped, positive-stranded RNA viruses whose name derives from their characteristic crown-like appearance in electron micrographs. Coronaviruses are classified as a family within the Nidovirales order, viruses that replicate using a nested set of mRNAs. The coronavirus subfamily is further classified into four genera: alpha, beta, gamma, and delta coronaviruses. The human coronaviruses (HCoVs) are in two of these genera: alpha coronaviruses (including HCoV-229E and HCoV-NL63) and beta coronaviruses (including HCoV-HKU1, HCoV-OC43, Middle East respiratory syndrome coronavirus (MERS-CoV), the severe acute respiratory syndrome coronavirus (SARS-CoV), and SARS-CoV-2).

In 2012, a novel coronavirus emerged in Saudi Arabia and became known as Middle East Respiratory Syndrome coronavirus (MERS-CoV). About half of reported cases of MERS-CoV infection have resulted in death and a majority of reported cases have occurred in older to middle age men. Only a small number of reported cases involved subjects with mild respiratory illness. Human to human transmission of MERS-CoV has been found to be possible, but very limited. Another novel coronavirus emerged in Wuhan, China in late 2019. This virus is known as SARS-CoV-2, 2019-nCoV, or Wuhan coronavirus, and it the cause of a worldwide pandemic in late 2019 and 2020.

Given the widespread transmission and potential health effects of these viruses, there is a need for drugs for treating norovirus and coronavirus infections.

SUMMARY

The present disclosure generally relates to methods of treating norovirus and coronavirus infections, to methods of inhibiting the replication of noroviruses and coronaviruses, to methods of reducing the amount of noroviruses and coronaviruses, and to compounds and compositions that can be employed for such methods.

The disclosure provides compounds as disclosed in Table A, and pharmaceutically acceptable salts thereof.

Also provided are compounds as disclosed in Table A wherein the moiety

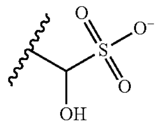 [SMILES: *C(O)S(=O)(=O)[O-]]

can be replaced with a moiety Z, wherein Z is $C_{1-6}$alkylene-OH, $C_{1-6}$alkylene-OH substituted with $PO(OCH_2CH_2)_2$, $C_{1-6}$alkylene-OH substituted with $SO_3H$, CHO, C(O)-(4-8 membered heterocycle having 1-3 ring heteroatoms selected from N, O, and S), or $CONR^AR^B$; and $R^A$ and $R^B$ are each independently H or $C_{1-6}$alkyl.

Further provided are methods of administering to a biological sample or patient a safe and effective amount of a compound as disclosed herein, e.g., a compound of Table A.

Also provided herein are methods of reducing the amount of noroviruses or coronaviruses in a biological sample or in a patient by administering to said biological sample or patient a safe and effective amount of a compound as disclosed herein, e.g., a compound of Table A.

Further provided are methods of treating or preventing a norovirus or coronavirus infection in a patient, comprising administering to said patient a safe and effective amount of a compound as disclosed herein, e.g., a compound of Table A.

Also provided are pharmaceutical compositions comprising a compound as disclosed herein, e.g., a compound of Table A, or a pharmaceutically acceptable salt thereof, and a pharmaceutically acceptable excipient, carrier, adjuvant or vehicle.

Also provided are uses of a compound described herein for inhibiting or reducing the replication of noroviruses or coronaviruses in a biological sample or patient, for reducing the amount of noroviruses or coronaviruses in a biological sample or patient, or for treating norovirus or coronavirus in a patient.

Further provided herein are uses of a compound described herein for the manufacture of a medicament for treating a norovirus or coronavirus infection in a patient, for reducing the amount of noroviruses or coronaviruses in a biological sample or in a patient, or for inhibiting the replication of noroviruses or coronaviruses in a biological sample or patient.

DETAILED DESCRIPTION

Provided herein are compounds, and their use in treating or preventing a norovirus or coronavirus infection. Also provided are uses of the compounds described herein, or pharmaceutically acceptable salts thereof, or pharmaceutically acceptable compositions comprising such a compound or a pharmaceutically acceptable salt thereof, for inhibiting the replication of norovirus or coronavirus viruses in a biological sample or in a patient, for reducing the amount of norovirus or coronavirus viruses (reducing viral titer) in a biological sample or in a patient, and for treating norovirus or coronavirus in a patient.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this disclosure, unless only one of the isomers is specifically indicated. Therefore, single stereochemical isomers as well as enantiomeric, diastereomeric, cis/trans, conformational, and rotational mixtures of the present compounds are within the scope of the disclosure. In some cases, the compounds disclosed herein are stereoisomers. "Stereoisomers" refer to compounds that differ in the chirality of one or more stereocenters. Stereoisomers include enantiomers and diastereomers. The compounds disclosed herein can exist as a single stereoisomer, or as a mixture of stereoisomers. Stereochemistry of the compounds shown herein indicate a relative stereochemistry, not absolute, unless discussed otherwise. As indicated herein, a single stereoisomer, diastereomer, or enantiomer refers to a compound that is at least more than 50% of the indicated stereoisomer, diastereomer, or enantiomer, and in some cases, at least 90% or 95% of the indicated stereoisomer, diastereomer, or enantiomer.

Unless otherwise indicated, all tautomeric forms of the compounds of the disclosure are within the scope of the disclosure.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this disclosure. Such compounds are useful, for example, as analytical tools or probes in biological assays. Such compounds, especially deuterium analogs, can also be therapeutically useful.

The compounds of the disclosure are defined herein by their chemical structures and/or chemical names. Where a compound is referred to by both a chemical structure and a chemical name, and the chemical structure and chemical name conflict, the chemical structure is determinative of the compound's identity.

Compounds

Provided herein are compounds as listed in Table A, or a pharmaceutically acceptable salt thereof.

TABLE A

| Compound no. | Structure |
|---|---|
| A1 | 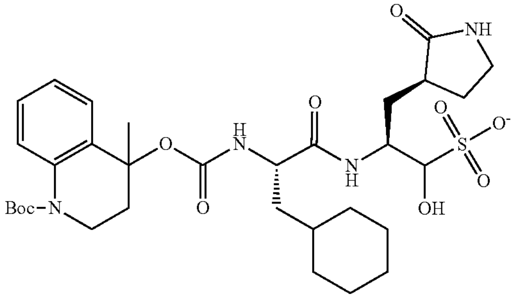 [SMILES: CC(C)(C)OC(=O)N1CCC(C)(OC(=O)N[C@@H](CC2CCCCC2)C(=O)N[C@@H](C[C@@H]2CCNC2=O)C(O)S(=O)(=O)[O-])c2ccccc21] |
| A2 | 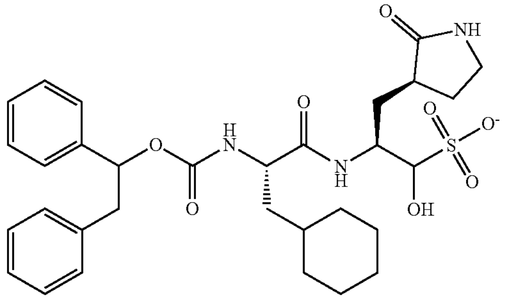 [SMILES: O=C(N[C@@H](CC1CCCCC1)C(=O)N[C@@H](C[C@@H]1CCNC1=O)C(O)S(=O)(=O)[O-])OC(Cc1ccccc1)c1ccccc1] |
| A3 | 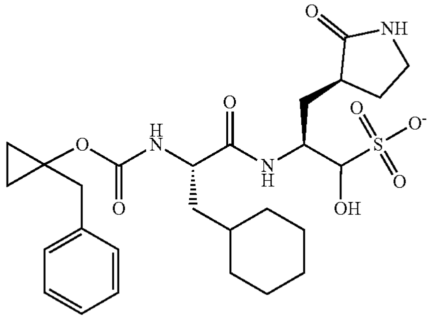 [SMILES: O=C(N[C@@H](CC1CCCCC1)C(=O)N[C@@H](C[C@@H]1CCNC1=O)C(O)S(=O)(=O)[O-])OC1(Cc2ccccc2)CC1] |

TABLE A-continued
| Compound no. | Structure |
|---|---|
| A4 | 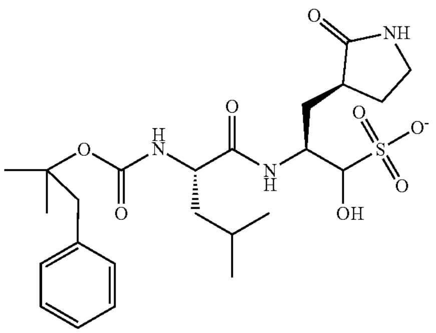 [SMILES: CC(C)C[C@H](NC(=O)OC(C)(C)Cc1ccccc1)C(=O)N[C@@H](C[C@@H]1CCNC1=O)C(O)S(=O)(=O)[O-]] |
| A5 | 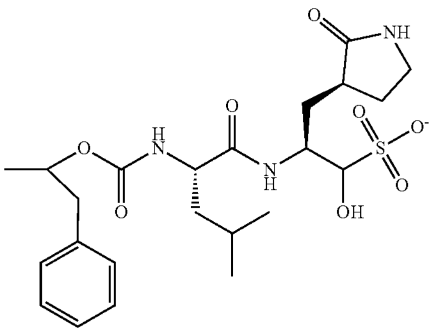 [SMILES: CC(C)C[C@H](NC(=O)OC(C)Cc1ccccc1)C(=O)N[C@@H](C[C@@H]1CCNC1=O)C(O)S(=O)(=O)[O-]] |
| A6 | 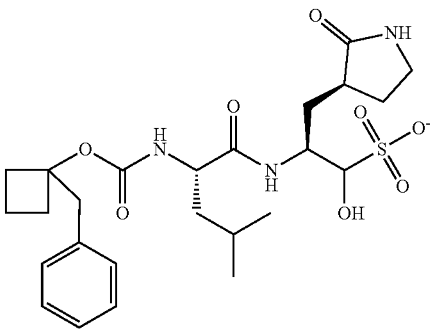 [SMILES: CC(C)C[C@H](NC(=O)OC1(Cc2ccccc2)CCC1)C(=O)N[C@@H](C[C@@H]1CCNC1=O)C(O)S(=O)(=O)[O-]] |
| A7 | 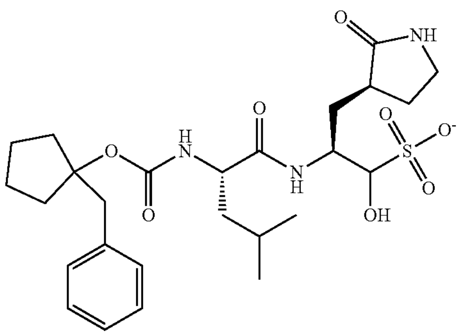 [SMILES: CC(C)C[C@H](NC(=O)OC1(Cc2ccccc2)CCCC1)C(=O)N[C@@H](C[C@@H]1CCNC1=O)C(O)S(=O)(=O)[O-]] |

TABLE A-continued
| Compound no. | Structure |
|---|---|
| A8 | 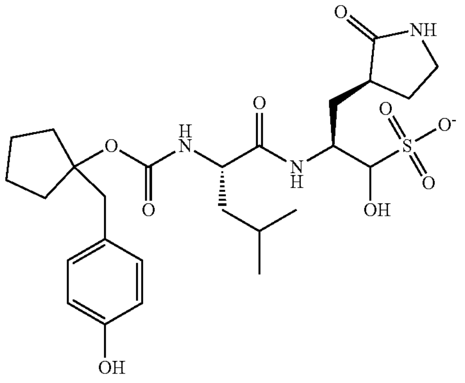 [SMILES: CC(C)C[C@H](NC(=O)OC1(Cc2ccc(O)cc2)CCCC1)C(=O)N[C@@H](C[C@@H]1CCNC1=O)C(O)S(=O)(=O)[O-]] |
| A9 | 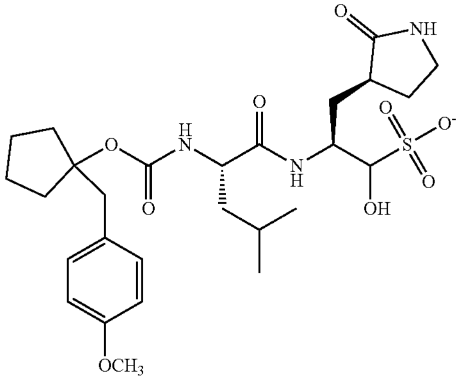 [SMILES: COc1ccc(CC2(OC(=O)N[C@@H](CC(C)C)C(=O)N[C@@H](C[C@@H]3CCNC3=O)C(O)S(=O)(=O)[O-])CCCC2)cc1] |
| A10 | 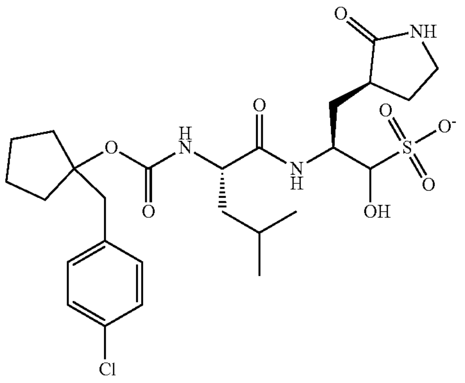 [SMILES: CC(C)C[C@H](NC(=O)OC1(Cc2ccc(Cl)cc2)CCCC1)C(=O)N[C@@H](C[C@@H]1CCNC1=O)C(O)S(=O)(=O)[O-]] |
| A11 | 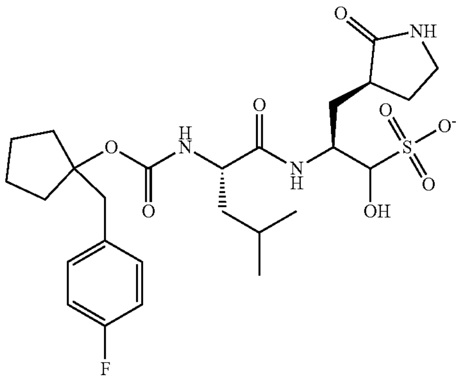 [SMILES: CC(C)C[C@H](NC(=O)OC1(Cc2ccc(F)cc2)CCCC1)C(=O)N[C@@H](C[C@@H]1CCNC1=O)C(O)S(=O)(=O)[O-]] |

TABLE A-continued
| Compound no. | Structure |
| --- | --- |
| A12 | 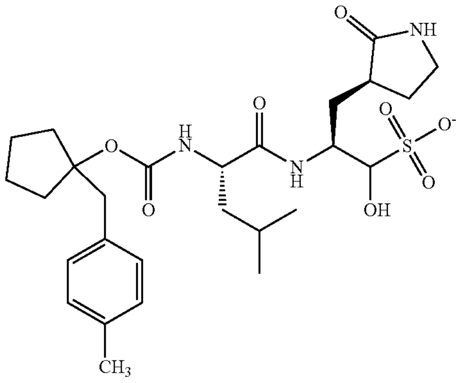 [SMILES: Cc1ccc(CC2(OC(=O)N[C@@H](CC(C)C)C(=O)N[C@@H](C[C@@H]3CCNC3=O)C(O)S(=O)(=O)[O-])CCCC2)cc1] |
| A13 | 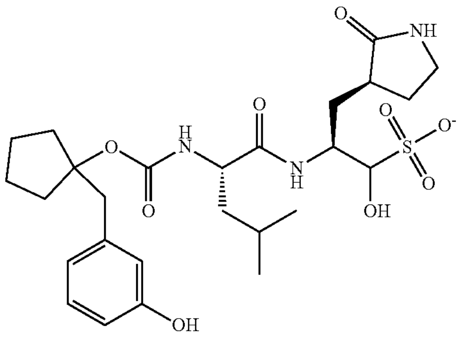 [SMILES: CC(C)C[C@H](NC(=O)OC1(Cc2cccc(O)c2)CCCC1)C(=O)N[C@@H](C[C@@H]1CCNC1=O)C(O)S(=O)(=O)[O-]] |
| A14 | 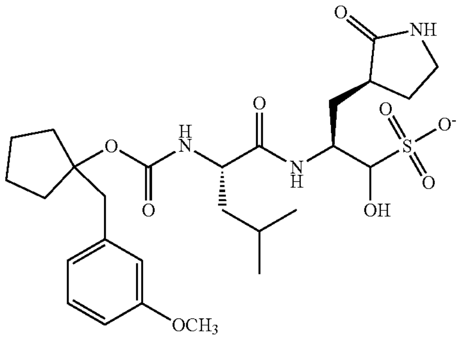 [SMILES: COc1cccc(CC2(OC(=O)N[C@@H](CC(C)C)C(=O)N[C@@H](C[C@@H]3CCNC3=O)C(O)S(=O)(=O)[O-])CCCC2)c1] |
| A15 | 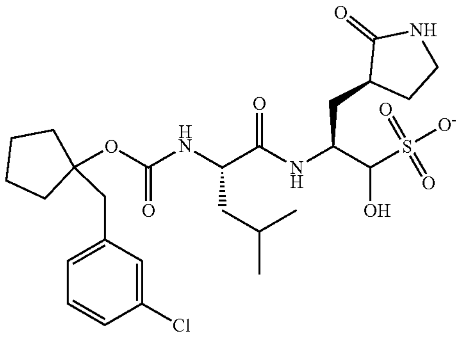 [SMILES: CC(C)C[C@H](NC(=O)OC1(Cc2cccc(Cl)c2)CCCC1)C(=O)N[C@@H](C[C@@H]1CCNC1=O)C(O)S(=O)(=O)[O-]] |

TABLE A-continued
| Compound no. | Structure |
|---|---|
| A16 | 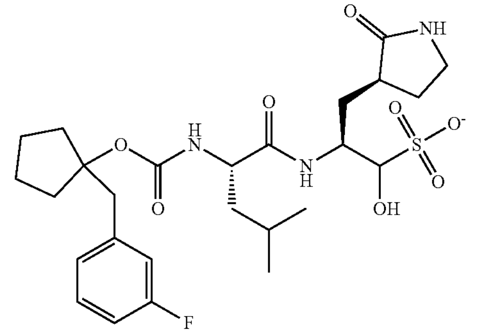 [SMILES: CC(C)C[C@H](NC(=O)OC1(Cc2cccc(F)c2)CCCC1)C(=O)N[C@@H](C[C@@H]1CCNC1=O)C(O)S(=O)(=O)[O-]] |
| A17 | 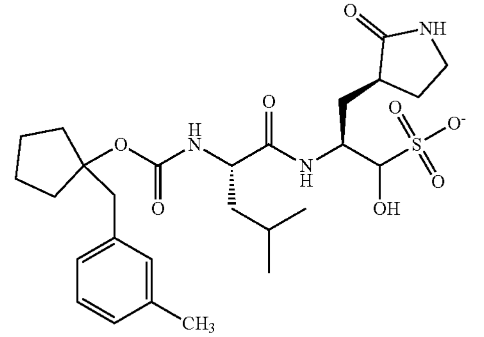 [SMILES: Cc1cccc(CC2(OC(=O)N[C@@H](CC(C)C)C(=O)N[C@@H](C[C@@H]3CCNC3=O)C(O)S(=O)(=O)[O-])CCCC2)c1] |
| A18 | 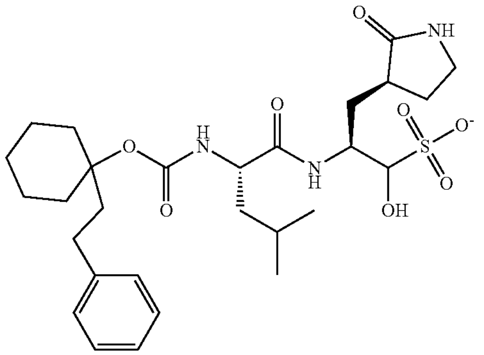 [SMILES: CC(C)C[C@H](NC(=O)OC1(CCc2ccccc2)CCCCC1)C(=O)N[C@@H](C[C@@H]1CCNC1=O)C(O)S(=O)(=O)[O-]] |
| A19 | 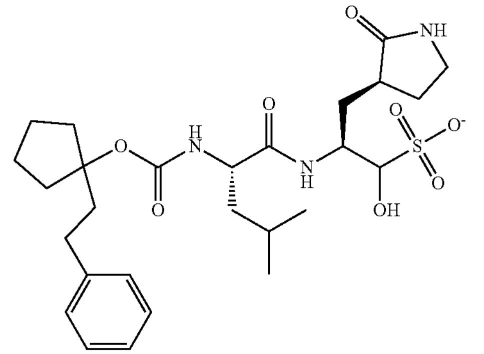 [SMILES: CC(C)C[C@H](NC(=O)OC1(CCc2ccccc2)CCCC1)C(=O)N[C@@H](C[C@@H]1CCNC1=O)C(O)S(=O)(=O)[O-]] |

TABLE A-continued
| Compound no. | Structure |
|---|---|
| A20 | 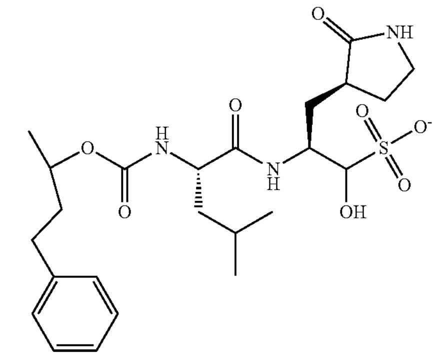 [SMILES: CC(C)C[C@H](NC(=O)OC(C)CCc1ccccc1)C(=O)N[C@@H](C[C@@H]1CCNC1=O)C(O)S(=O)(=O)[O-]] |
| A21 | 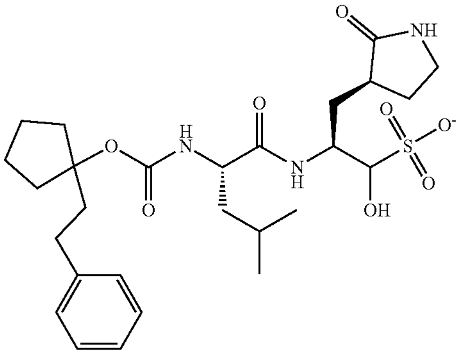 [SMILES: CC(C)C[C@H](NC(=O)OC1(CCc2ccccc2)CCCC1)C(=O)N[C@@H](C[C@@H]1CCNC1=O)C(O)S(=O)(=O)[O-]] |
| A22 | 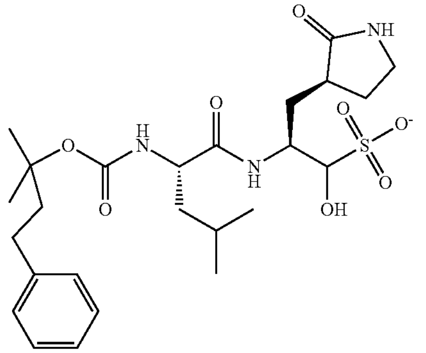 [SMILES: CC(C)C[C@H](NC(=O)OC(C)(C)CCc1ccccc1)C(=O)N[C@@H](C[C@@H]1CCNC1=O)C(O)S(=O)(=O)[O-]] |
| A23 | 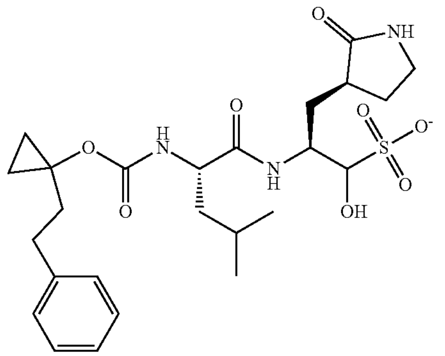 [SMILES: CC(C)C[C@H](NC(=O)OC1(CCc2ccccc2)CC1)C(=O)N[C@@H](C[C@@H]1CCNC1=O)C(O)S(=O)(=O)[O-]] |

TABLE A-continued
| Compound no. | Structure |
|---|---|
| A24 | 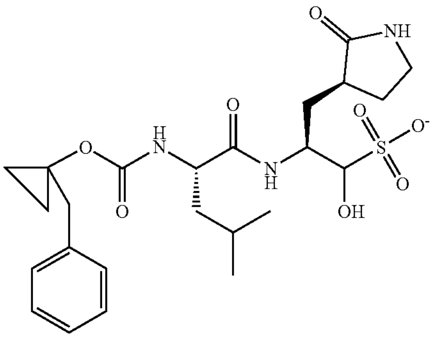 [SMILES: CC(C)C[C@H](NC(=O)OC1(Cc2ccccc2)CC1)C(=O)N[C@@H](C[C@@H]1CCNC1=O)C(O)S(=O)(=O)[O-]] |
| A25 | 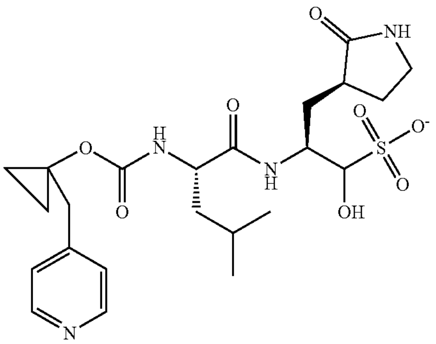 [SMILES: CC(C)C[C@H](NC(=O)OC1(Cc2ccncc2)CC1)C(=O)N[C@@H](C[C@@H]1CCNC1=O)C(O)S(=O)(=O)[O-]] |
| A26 | 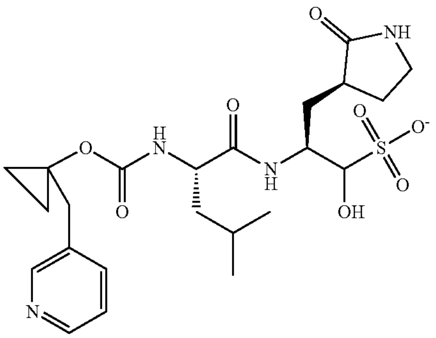 [SMILES: CC(C)C[C@H](NC(=O)OC1(Cc2cccnc2)CC1)C(=O)N[C@@H](C[C@@H]1CCNC1=O)C(O)S(=O)(=O)[O-]] |
| A27 | 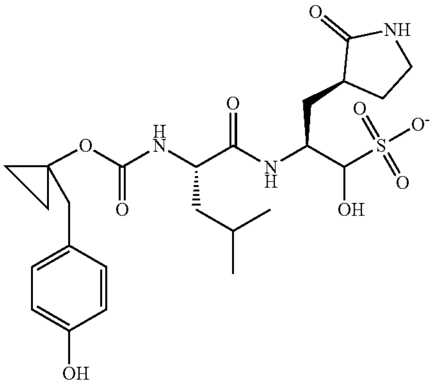 [SMILES: CC(C)C[C@H](NC(=O)OC1(Cc2ccc(O)cc2)CC1)C(=O)N[C@@H](C[C@@H]1CCNC1=O)C(O)S(=O)(=O)[O-]] |

TABLE A-continued
| Compound no. | Structure |
|---|---|
| A28 | 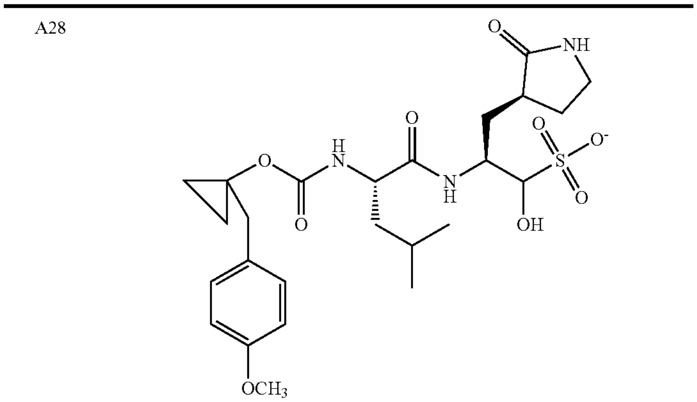 |
| A29 | 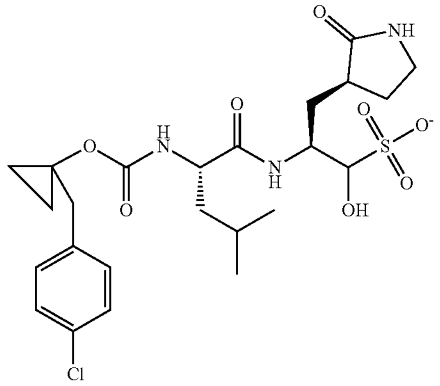 [SMILES: CC(C)C[C@H](NC(=O)OC1(Cc2ccc(Cl)cc2)CC1)C(=O)N[C@@H](C[C@@H]1CCNC1=O)C(O)S(=O)(=O)[O-]] |
| A30 | 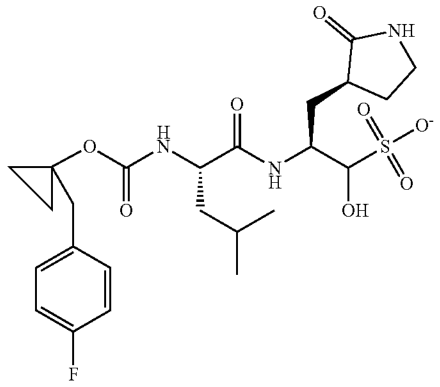 [SMILES: CC(C)C[C@H](NC(=O)OC1(Cc2ccc(F)cc2)CC1)C(=O)N[C@@H](C[C@@H]1CCNC1=O)C(O)S(=O)(=O)[O-]] |
| A31 | 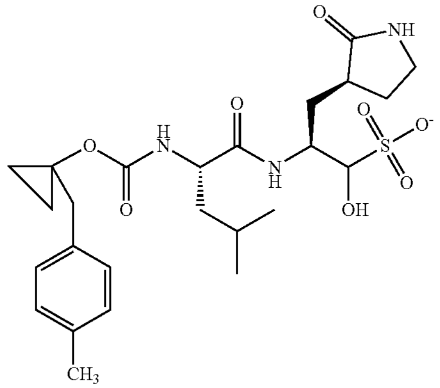 [SMILES: Cc1ccc(CC2(OC(=O)N[C@@H](CC(C)C)C(=O)N[C@@H](C[C@@H]3CCNC3=O)C(O)S(=O)(=O)[O-])CC2)cc1] |

TABLE A-continued
| Compound no. | Structure |
|---|---|
| A32 | 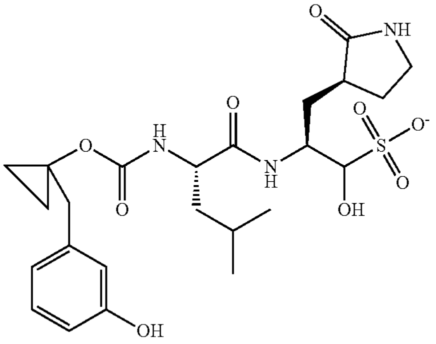 [SMILES: CC(C)C[C@H](NC(=O)OC1(Cc2cccc(O)c2)CC1)C(=O)N[C@@H](C[C@@H]1CCNC1=O)C(O)S(=O)(=O)[O-]] |
| A33 | 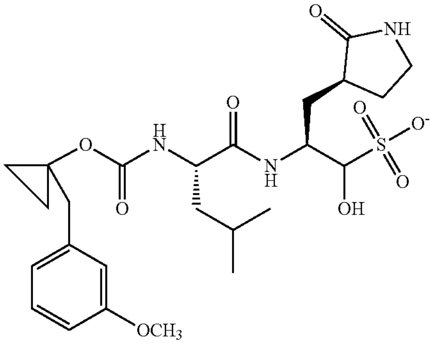 [SMILES: COc1cccc(CC2(OC(=O)N[C@@H](CC(C)C)C(=O)N[C@@H](C[C@@H]3CCNC3=O)C(O)S(=O)(=O)[O-])CC2)c1] |
| A34 | 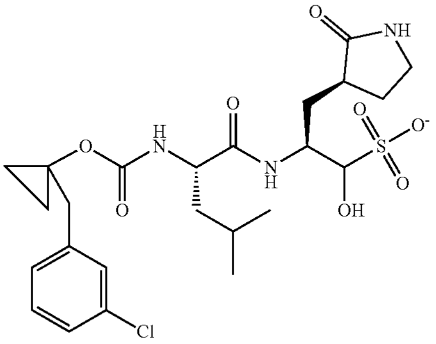 |
| A35 | 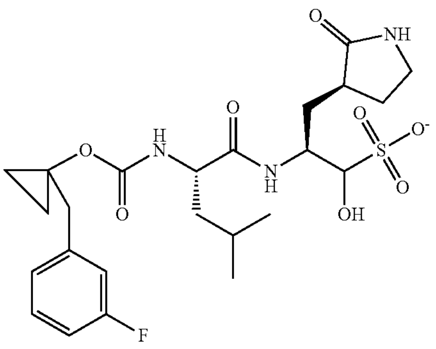 [SMILES: CC(C)C[C@H](NC(=O)OC1(Cc2cccc(F)c2)CC1)C(=O)N[C@@H](C[C@@H]1CCNC1=O)C(O)S(=O)(=O)[O-]] |

TABLE A-continued
| Compound no. | Structure |
| --- | --- |
| A36 | 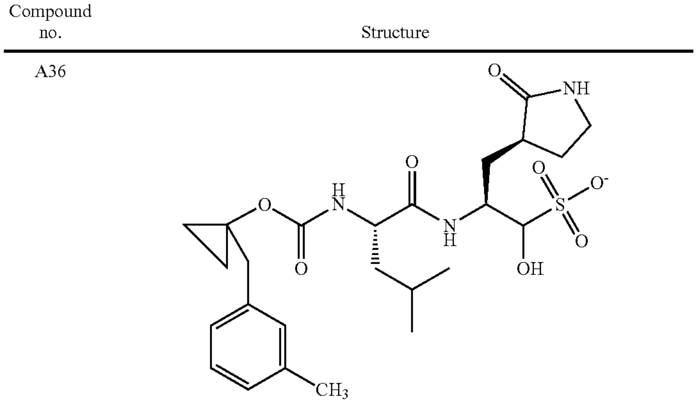 |
| A37 | 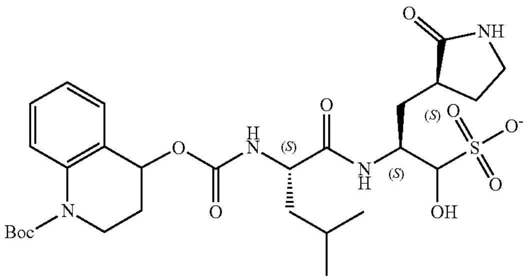 |
| A38 | 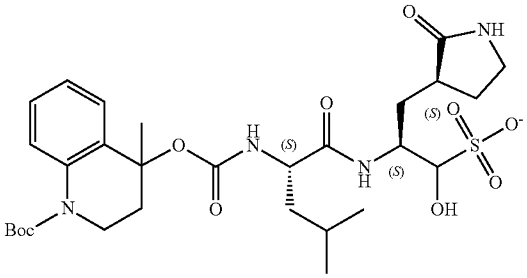 |
| A39 | 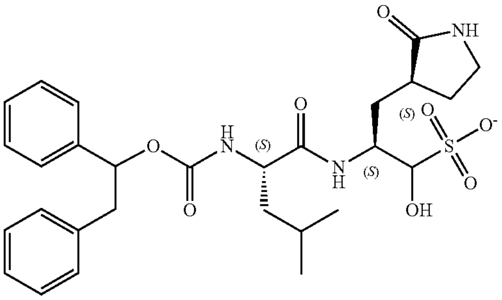 |
| A40 | 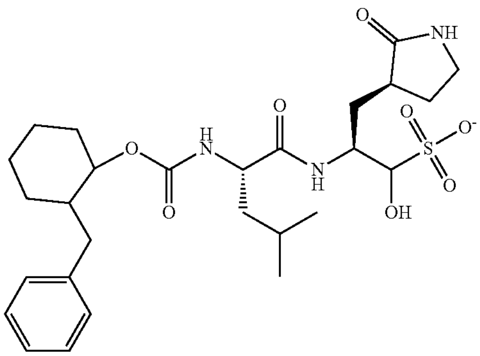 [SMILES: CC(C)C[C@H](NC(=O)OC1CCCCC1Cc1ccccc1)C(=O)N[C@@H](C[C@@H]1CCNC1=O)C(O)S(=O)(=O)[O-]] |

TABLE A-continued

| Compound no. | Structure |
|---|---|
| A41 | 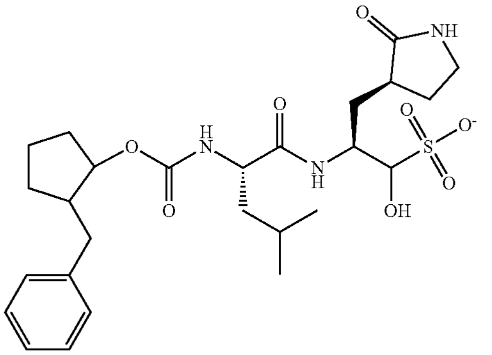 [SMILES: CC(C)C[C@H](NC(=O)OC1CCCC1Cc1ccccc1)C(=O)N[C@@H](C[C@@H]1CCNC1=O)C(O)S(=O)(=O)[O-]] |
| A42 | 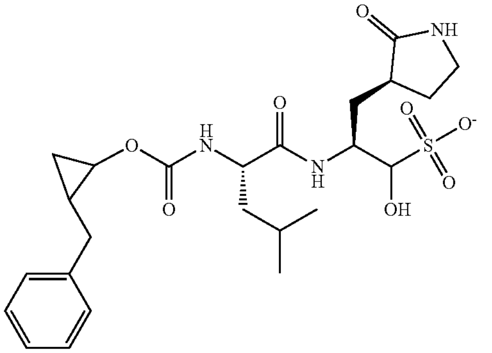 [SMILES: CC(C)C[C@H](NC(=O)OC1CC1Cc1ccccc1)C(=O)N[C@@H](C[C@@H]1CCNC1=O)C(O)S(=O)(=O)[O-]] |

In the compounds of Table A, it is also contemplated that the moiety

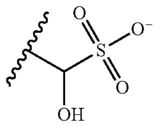 [SMILES: *C(O)S(=O)(=O)[O-]]

can be replaced with a moiety Z, wherein

Z is $C_{1-6}$alkylene-OH, $C_{1-6}$alkylene-OH substituted with $PO(OCH_2CH_2)_2$, $C_{1-6}$alkylene-OH substituted with $SO_3H$, CHO, C(O)-(4-8 membered heterocycle having 1-3 ring heteroatoms selected from N, O, and S), or $CONR^AR^B$; and $R^A$ and $R^B$ are each independently H or $C_{1-6}$alkyl.

The compounds disclosed herein can be useful as inhibitors of norovirus or coronavirus replication in biological samples or in a patient. These compounds can also be useful in reducing the amount of noroviruses or coronaviruses (viral titer) in a biological sample or in a patient. They can also be useful for therapeutic and prophylactic treatment of infections caused by the noroviruses or coronaviruses in a biological sample or in a patient.

Pharmaceutically Acceptable Salts

The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the disclosure or intermediates thereof.

As used herein, the term “pharmaceutically acceptable salt” refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that a compound disclosed herein can be present as a mixture/combination of different pharmaceutically acceptable salts. Also contemplated are mixtures/combinations of compounds in free form and pharmaceutically acceptable salts.

Pharmaceutical Compositions

The compounds described herein can be formulated into pharmaceutical compositions that further comprise a pharmaceutically acceptable carrier, diluent, adjuvant or vehicle. In embodiments, the present disclosure relates to a pharmaceutical composition comprising a compound described above or salt thereof, and a pharmaceutically acceptable carrier, diluent, adjuvant or vehicle. In embodiments, the pharmaceutical composition comprises a safe and effective amount of a compound as disclosed herein or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating a norovirus or coronavirus virus infection in a patient. The term "prophylactically effective amount" refers to an amount effective in preventing and/or substantially lessening the chances or the size of norovirus or coronavirus virus infection outbreak.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this disclosure. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Formulations for Pulmonary Delivery

In some embodiments, the pharmaceutical compositions disclosed herein are adapted to be administered to the lower respiratory tract (e.g., the lungs) directly through the airways by inhalation. Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminum foil for use in an inhaler or insufflators. Each capsule or cartridge may generally contain e.g., from about 10 mg to about 100 g of each active compound. Alternatively, the composition may be presented without excipients.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360, and 5,590,645 (all illustrating the "Diskus" device), or GB2i78965, GB2129691, GB2169265, U.S. Pat. Nos. 4,778,054, 4,811,731 and 5,035,237 (which illustrate the "Diskhaler" device), or EP 69715 ("Turbuhaler" device), or GB 2064336 and U.S. Pat. No. 4,353,656 ("Rotahaler" device).

Spray compositions for topical delivery to the lung by inhalation may be formulated as aqueous solutions or suspensions or as aerosols delivered from pressurized packs, such as a metered dose inhaler (MDI), with the use of a suitable liquefied propellant, including hydrofluoroalkanes such as dichlorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof. Aerosol compositions suitable for inhalation can be presented either as suspensions or as solutions.

Medicaments for administration by inhalation typically have a controlled particle size. The optimum particle size for inhalation into the bronchial system is usually about 1 to about 10 μm, and in some embodiments, from about 2 to about 5 μm. Particles having a size above about 20 μm are generally too large when inhaled to reach the small airways. To achieve these particle sizes the particles of the active ingredient may be subjected to a size reducing process such as micronization. The desired size fraction may be separated out by air classification or sieving. Preferably, the particles will be crystalline.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulization may be formulated with an aqueous vehicle with the addition of agents such as acid or alkali, buffer salts, isotonic adjusting agents or antimicrobial agents. They may be sterilized by filtration or heating in an autoclave, or presented as a non-sterile product. Nebulizers supply the aerosol as a mist created from an aqueous formulation.

In some embodiments, the pharmaceutical compositions disclosed herein can be formulated with supplementary active ingredients.

In some embodiments, the pharmaceutical composition disclosed herein is administered from a dry powder inhaler. In other embodiments, the pharmaceutical composition disclosed herein is administered by an aerosol dispensing device, optionally in conjunction with an inhalation chamber such as the "Volumatic"® inhalation chamber.

The carrier can be a solvent or dispersion medium containing, for example, water, ethanol, polyol (for example, glycerol, propylene glycol and liquid polyethylene glycol, and the like), suitable mixtures thereof, and/or vegetable oils. The proper fluidity can be maintained, for example, by the use of a coating such as, for example, lecithin, by the maintenance of the required particle size in the case of dispersion and by the use of surfactants. Preventing the action of microorganisms in the compositions disclosed herein is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, a pharmaceutical composition can be within a matrix which controls the release of the composition. In some embodiments, the matrix can comprise lipid, polyvinyl alcohol, polyvinyl acetate, polycaprolactone, poly(glycolic)acid, poly(lactic)acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and combinations thereof and other polymers such as those disclosed, for example, in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. In these embodiments, the matrix sustainedly releases the drug.

Pharmaceutically acceptable carriers and/or diluents may also include any solvents, dispersion media, coatings, antibacterials and/or antifungals, isotonic and absorption delaying agents and the like. The use of such media and agents for pharmaceutically active substances is well known in the art. Except insofar as any conventional medium or agent is incompatible with the active ingredient, use thereof in the pharmaceutical compositions is contemplated.

The pharmaceutical compositions can be formulated for administration in accordance with conventional techniques. See, e.g., Remington, The Science and Practice of Pharmacy (20th Ed. 2000). For example, the intranasal pharmaceutical compositions of the present disclosure can be formulated as an aerosol (this term includes both liquid and dry powder aerosols). Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles (e.g., lyophilized, freeze dried, etc.) can likewise be produced with any solid particulate medicament aerosol generator, by techniques known in the pharmaceutical art. As another example, the pharmaceutical compositions can be formulated as an on-demand dissolvable form, which provides a lyophilized portion of the pharmaceutical composition and a dissolving solution portion of the pharmaceutical composition.

In some embodiments, the pharmaceutical composition is in the form of an aqueous suspension, which can be prepared from solutions or suspensions. With respect to solutions or suspensions, dosage forms can be comprised of micelles of lipophilic substances, liposomes (phospholipid vesicles/membranes) and/or a fatty acid (e.g., palmitic acid). In particular embodiments, the pharmaceutical composition is a solution or suspension that is capable of dissolving in the fluid secreted by mucous membranes of the epithelium of the tissue to which it is administered, applied and/or delivered, which can advantageously enhance absorption.

The pharmaceutical composition can be an aqueous solution, a nonaqueous solution or a combination of an aqueous and nonaqueous solution. Suitable aqueous solutions include, but are not limited to, aqueous gels, aqueous suspensions, aqueous microsphere suspensions, aqueous microsphere dispersions, aqueous liposomal dispersions, aqueous micelles of liposomes, aqueous microemulsions, and any combination of the foregoing, or any other aqueous solution that can dissolve in the fluid secreted by the mucosal membranes of the nasal cavity. Exemplary nonaqueous solutions include, but are not limited to, nonaqueous gels, nonaqueous suspensions, nonaqueous microsphere suspensions, nonaqueous microsphere dispersions, nonaqueous liposomal dispersions, nonaqueous emulsions, nonaqueous microemulsions, and any combination of the foregoing, or any other nonaqueous solution that can dissolve or mix in the fluid secreted by mucosal membranes.

Examples of powder formulations include, without limitation, simple powder mixtures, micronized powders, freeze dried powder, lyophilized powder, powder microspheres, coated powder microspheres, liposomal dispersions, and any combination of the foregoing. Powder microspheres can be formed from various polysaccharides and celluloses, which include without limitation starch, methylcellulose, xanthan gum, carboxymethylcellulose, hydroxypropyl cellulose, carbomer, alginate polyvinyl alcohol, acacia, chitosans, and any combination thereof.

In particular embodiments, the composition is one that is at least partially, or even substantially (e.g., at least 80%, 90%, 95% or more) soluble in the fluids that are secreted by mucosa so as to facilitate absorption. Alternatively or additionally, the composition can be formulated with a carrier and/or other substances that foster dissolution of the agent within secretions, including without limitation fatty acids (e.g., palmitic acid), gangliosides (e.g., GM-1), phospholipids (e.g., phosphatidylserine), and emulsifiers (e.g., polysorbate 80).

Those skilled in the art will appreciate that for intranasal administration or delivery, because the volume of the pharmaceutical composition administered is generally small, nasal secretions may alter the pH of the administered dose since the range of pH in the nasal cavity can be as wide as 5 to 8. Such alterations can affect the concentration of un-ionized drug available for absorption. Accordingly, in representative embodiments, the pharmaceutical composition further comprises a buffer to maintain or regulate pH in situ. Typical buffers include, but are not limited to, ascorbate, acetate, citrate, prolamine, carbonate, and phosphate buffers.

In embodiments, the pH of the pharmaceutical composition is selected so that the internal environment of the mucosal tissue after administration is on the acidic to neutral side, which (1) can provide the active compound in an un-ionized form for absorption, (2) prevents growth of pathogenic bacteria, which is more likely to occur in an alkaline environment, and (3) reduces the likelihood of irritation of the mucosa.

For liquid and powder sprays or aerosols, the pharmaceutical composition can be formulated to have any suitable and desired particle or droplet size. In illustrative embodiments, the majority and/or the mean size of the particles or droplets range from equal to or greater than about 1, 2.5, 5, 10, 15 or 20 microns and/or equal to or less than about 25, 30, 40, 45, 50, 60, 75, 100, 125, 150, 175, 200, 225, 250, 275, 300, 325, 350, 375, 400, or 425 microns (including all combinations of the foregoing). Representative examples of suitable ranges for the majority and/or mean particle or droplet size include, without limitation, from about 5 to 100 microns, from about 10 to 60 microns, from about 175 to 325 microns, and from about 220 to 300 microns which facilitate the deposition of a safe and effective amount of the active compound, for example, in the nasal cavity (e.g., in the upper third of the nasal cavity, the superior meatus, the olfactory region and/or the sinus region to target the olfactory neural pathway). In general, particles or droplets smaller than about 5 microns will be deposited in the trachea or even the lung, whereas particles or droplets that are about 50 microns or larger generally do not reach the nasal cavity and are deposited in the anterior nose.

International patent publication WO 2005/023335 (Kurve Technology, Inc.) describes particles and droplets having a diameter size suitable for the practice of representative embodiments of pharmaceutical compositions disclosed herein. In particular embodiments, the particles or droplets have a mean diameter of about 5 to 30 microns, about 10 to 20 microns, about 10 to 17 microns, about 10 to 15 microns, about 12 to 17 microns, about 10 to 15 microns or about 10 to 12 microns. The particles can "substantially" have a mean diameter or size as described herein, i.e., at least about 50%, 60%, 70%, 80%, 90% or 95 or more of the particles are of the indicated diameter or size range.

The pharmaceutical composition can be delivered as a nebulized or atomized liquid having a droplet size as described above.

According to particular embodiments of this disclosure that comprise methods of intranasal delivery, it can be desirable to prolong the residence time of the pharmaceutical composition in the nasal cavity (e.g., in the upper third of the nasal cavity, the superior meatus, the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl), which are agents that enhance residence time in the nasal cavity. As a further approach, increasing the viscosity of the formulation can also provide a means of prolonging contact of the agent with the nasal epithelium. The pharmaceutical composition can be formulated as a nasal emulsion, ointment or gel, which offers advantages for local application because of their viscosity.

Moist and highly vascularized membranes can facilitate rapid absorption; consequently, the pharmaceutical composition can optionally comprise a humectant, particularly in the case of a gel-based composition so as to assure adequate intranasal moisture content. Examples of suitable humectants include but are not limited to glycerin or glycerol, mineral oil, vegetable oil, membrane conditioners, soothing agents, and/or sugar alcohols (e.g., xylitol, sorbitol; and/or mannitol). The concentration of the humectant in the pharmaceutical composition will vary depending upon the agent selected and the formulation.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g., EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol and benzalkonium chloride, and combinations of the foregoing. The concentration of the preservative will vary depending upon the preservative used, the compound being formulated, the formulation, and the like. In representative embodiments, the preservative is present in an amount of about 2% by weight or less.

The pharmaceutical compositions described herein can optionally contain an odorant, e.g., as described in EP 0 504 263 B1, to provide a sensation of odor, to aid in inhalation of the composition so as to promote delivery to the olfactory region and/or to trigger transport by the olfactory neurons.

As another option, the composition can comprise a flavoring agent, e.g., to enhance the taste and/or acceptability of the composition to the subject.

Porous Particles for Pulmonary Administration

In some embodiments, the particles are porous, so that they have an appropriate density to avoid deposition in the back of the throat when administered via an inhaler. The combination of relatively large particle size and relatively low density avoids phagocytosis in the lungs, provides appropriately targeted delivery, avoids systemic delivery of the components, and provides a high concentration of the components in the lung.

Representative methods for preparing such particles, and for delivering such particles, are described, for example, in U.S. Pat. No. 7,384,649, entitled, “Particulate compositions for pulmonary delivery,” U.S. Pat. No. 7,182,961, entitled “Particulate compositions for pulmonary delivery,” U.S. Pat. No. 7,146,978, entitled, “Inhalation device and method,” U.S. Pat. No. 7,048,908, entitled “Particles for inhalation having sustained release properties,” U.S. Pat. No. 6,956,021, entitled “Stable spray-dried protein formulations,” U.S. Pat. No. 6,766,799, entitled “Inhalation device,” and U.S. Pat. No. 6,732,732, entitled “Inhalation device and method.”

Additional patents disclosing such particles include U.S. Pat. No. 7,279,182, entitled “Formulation for spray-drying large porous particles,” U.S. Pat. No. 7,252,840, entitled “Use of simple amino acids to form porous particles,” U.S. Pat. No. 7,032,593, entitled “Inhalation device and method,” U.S. Pat. No. 7,008,644, entitled “Method and apparatus for producing dry particles,” U.S. Pat. No. 6,848,197, entitled “Control of process humidity to produce large, porous particles,” and U.S. Pat. No. 6,749,835, entitled “Formulation for spray-drying large porous particles.”

U.S. Pat. No. 7,678,364, entitled “Particles for inhalation having sustained release properties,” discloses methods for delivering particles to the pulmonary system comprising: administering to the respiratory tract of a patient in need of treatment, prophylaxis or diagnosis a safe and effective amount of a dry powder comprising: a) a multivalent metal cation which is complexed with a therapeutic, prophylactic or diagnostic agent; b) a pharmaceutically acceptable carrier; and c) a multivalent metal cation-containing component wherein the dry powder is spray-dried and has a total amount of multivalent metal cation which is about 10% w/w or more of the total weight of the agent, a tap density of about 0.4 $g/cm^3$ or less, a median geometric diameter of from about 5 micrometers to about 30 micrometers and an aerodynamic diameter of from about 1 to about 5 microns.

The amount of the compounds described herein, or salts thereof, present in the particles can range from about 0.1 weight % to about 95 weight %, though in some cases, can even be as high as 100%. For example, from about 1 to about 50%, such as from about 5 to about 30%. Particles in which the compound is distributed throughout a particle can be preferred.

In some embodiments, the particles include a surfactant other than the phospholipids described above. As used herein, the term “surfactant” refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to particles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles disclosed herein include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85); Tween® 80 and tyloxapol.

The surfactant can be present in the particles in an amount ranging from about 0 to about 5 weight %. Preferably, it can be present in the particles in an amount ranging from about 0.1 to about 1.0 weight %.

Particles that have a tap density less than about 0.4 g/$cm^3$, median diameters of at least about 5 μm, and an aerodynamic diameter of from about 1 μm to about 5 μm, or from about 1 μm to about 3 μm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

Liposomal Delivery

The compositions described herein are advantageously delivered to the lungs, so as to provide the compounds at the site of an actual or potential norovirus or coronavirus infection. This can be accomplished by pulmonary delivery via metered-dose inhalers or other pulmonary delivery devices, and also by lodging particles in the capillary beds surrounding the alveoli in the lungs.

Nanocarriers, such as liposomes, including small unilamellar vesicles, show several advantages over other conventional approaches for delivering drugs to the lungs, including prolonged drug release and cell-specific targeted drug delivery. Nano-sized drug carriers can also be advantageous for delivering poorly water soluble drugs, and certain of the compounds described herein are poorly water-soluble. Additional advantages include their ability to provide controlled release, protection from metabolism and degradation, decreased drug toxicity and targeting capabilities.

The liposomes (preferably unilamellar vesicles) have a size less than 200 nm as measured by dynamic light scattering, and preferably characterized by being comprised of chemically pure synthetic phospholipids, most preferably having aliphatic side chains of a length of at least 16 carbons, and containing one or more of the compounds described herein, or a pharmaceutically acceptable salt thereof, sufficient to preferentially deliver (i.e., target) a quantity of the compounds thereof to the capillary beds surrounding the alveoli. Vesicle diameter can be measured, for example, by dynamic light scattering using a helium-neon 100 mW NEC gas laser and a Malvern K7027 correlator, ideally with at least two or three measurements made for each for each size determination.

The expression "chemically pure phospholipids" is meant to define phospholipids which are essentially free of deleterious detergent moieties and impurities which cause aggregation of small unilamellar vesicles (SUVs) formed therefrom, and which are more than 97% pure. Preferably, the liposomes have a diameter predominantly of from about 50 to about 160 nm, are essentially neutral in charge, and incorporate phospholipids having a side chain length of from 16 to 18 carbon atoms. More preferably, the liposomes are prepared from distearoyl phosphatidylcholine (DSPC) and include cholesterol (most preferably in an amount of from 10 to 50% of total lipid) as a vesicle stabilizer.

It can also be advantageous that the liposomes have a melting point above body temperature (i.e., above 37° C.). For this reason, it can be advantageous to use pure phospholipids, preferably ones that are saturated, and have a carbon chain length of at least 16 carbons, preferably between 16 and 18 carbons. Distearoylphosphatidyl choline (DSPC) is a preferred phospholipid.

Cholesterol helps to stabilize the liposomes, and is preferably added in a sufficient amount to provide liposome stability. Most preferably, the liposomes further comprise a pegylated phospholipid, such as DSPEPEG. The method involves introducing into a patient's bloodstream an amount of liposomes, of a size of less than 200 nm (preferably unilamellar vesicles) and preferably characterized by being comprised of chemically pure synthetic phospholipids, most preferably having aliphatic side chains of a length of at least 16 carbons, and containing the compounds described herein, or a pharmaceutically acceptable salt or prodrug thereof, sufficient to preferentially deliver (i.e., target) a quantity of the compounds to the capillary beds in the lungs, surrounding the alveoli.

The compounds described herein can be combined with other anti-norovirus or anti-coronavirus agents. Such additional agents can also be present in the liposomes, can be present in different liposomes, or can be co-administered via a different route.

The liposomes include one or more of the compounds described herein, or a pharmaceutically acceptable salt thereof, and can optionally include other anti-norovirus or anti-coronavirus agents. The liposomes can be prepared by dissolving the phospholipid and cholesterol in an appropriate organic solvent, such as chloroform, and evaporating the solvent to form a lipid film. If an ionophore is employed to load the compounds described herein into the liposomes, the ionophore may be added to the lipid solution before evaporation. The dried lipid film is then rehydrated in an appropriate aqueous phase, such as phosphate-buffered saline or other physiologically appropriate solution. Water-soluble drugs or therapeutic agents may be contained in the hydrating solution, although if remote loading is desired a loading agent such as a chelating agent described above may be added to the hydrating solution to be encapsulated within the inner aqueous space of the liposome.

Upon the addition of the hydrating solution, liposomes of varying size spontaneously form and encapsulate a portion of the aqueous phase. Thereafter, the liposomes and suspending aqueous solution are subjected to a shear force such as extrusion, sonication, or processing through a homogenizer according to the method described in U.S. Pat. No. 4,753,788; to produce vesicles within the specified size.

The liposomes can then be processed to remove undesirable compounds from the suspending solution, for example, un-encapsulated drug, which may be accomplished through processes such as gel chromatography or ultrafiltration.

The use of liposomes in dry powder aerosols for targeted lung delivery is described, for example, in Willis et al., *Lung*, June 2012, 190(3):251-262. One advantage is that the phospholipids used to prepare the liposomes are similar to endogenous lung surfactant.

Routes of Administration and Dosages

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, to the pulmonary system, such as by using an inhaler, such as a metered dose inhaler (MDI), or the like, depending on the severity of the infection being treated. In some embodiments, the compound or composition disclosed herein is administered orally, via inhalation, or intravenously.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topical application also includes the use of transdermal patches.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the disclosure can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Methods of Treatment

Provided herein are uses of a compound described herein as a therapeutic agent. The compounds described herein or pharmaceutically acceptable salts thereof can be used to reduce viral titer in a biological sample (e.g. an infected cell culture) or in humans (e.g. lung viral titer in a patient). The compounds described herein or pharmaceutically acceptable salts thereof can be used in methods of treating viral infections. Non-limiting examples of viral infections which can be treated with the compounds described herein or their pharmaceutically acceptable salts include coronavirus infections, calicivirus infections, and picornavirus infections.

Non-limiting examples of calicivirus infections include norovirus mediated conditions and norovirus infection. The terms "norovirus mediated condition", "norovirus infection", and "norovirus", as used herein, are used interchangeably to mean the disease caused by an infection with a norovirus.

Noroviruses are infectious viruses that cause gastroenteritis in mammals. Noroviruses are RNA viruses of the family Caliciviridae, which comprises seven genogroups: GI, GII, GIII, GIV, GV, GVI, and GVII. Genogroup II, the most prevalent human genogroup, presently contains 19 genotypes. Genogroups I, II and IV infect humans, whereas genogroup III infects bovine species, and genogroup V has recently been isolated in mice. The two groups most associated with gastroenteritis in humans are genogroup I (GI), which includes Norwalk virus, Desert Shield virus and Southampton virus; and genogroup II (GII), which includes Bristol virus, Lordsdale virus, Toronto virus, Mexico virus, Hawaii virus and Snow Mountain virus.

In some embodiments, the compounds used herein are for treatment of noroviruses which are associated with gastroenteritis. In some embodiments, noroviruses are associated with Norwalk virus. In some embodiments, noroviruses are associated with HuNV GGII.4.

In some embodiments, the compounds disclosed herein can be used in the treatment of norovirus, wherein the compound binds to free virus, or inhibits a norovirus protease. In some cases, the compound can target both (free virus and protease).

In humans, common symptoms of norovirus are nausea, vomiting, watery diarrhea, abdominal pain, and in some cases, loss of taste. Norovirus can establish a long term infection in people who are immunocompromised. In severe cases, persistent infections can lead to norovirus-associated enteropathy, intestinal villous atrophy, and malabsorption. Norovirus-associated gastroenteritis is also called "winter vomiting bug".

A person usually develops symptoms of gastroenteritis 12 to 48 hours after being exposed to norovirus. General lethargy, weakness, muscle aches, headaches, and low-grade fevers may occur.

The terms "coronavirus mediated condition" and "coronavirus infection" as used herein, are used interchangeably to mean the disease caused by an infection with a coronavirus. Non-limiting examples of coronaviruses include severe acute respiratory syndrome-related coronavirus (SARS), Middle East respiratory syndrome-related coronavirus (MERS), and SARS-CoV-2 virus (also known as 2019-nCoV, or Wuhan coronavirus). Non-limiting examples of coronavirus mediated conditions or coronavirus infections include SARS, MERS, and COVID-19.

Coronaviruses are a family of viruses that cause diseases in mammals and birds. Coronaviruses are in the subfamily Orthocoronavirinae in the family Coronaviridae, in the order Nidovirales. There are four main genera of coronaviruses, known as alpha, beta, gamma, and delta. Coronaviruses that affect humans include Human coronavirus 229E (HCoV-229E), Human coronavirus OC43 (HCoV-OC43), Severe acute respiratory syndrome-related coronavirus (SARS-CoV), Human coronavirus NL63 (HCoV-NL63, New Haven coronavirus), Human coronavirus HKU1, Middle East respiratory syndrome-related coronavirus (MERS-CoV, previously known as novel coronavirus 2012 and HCoV-EMC), and SARS-CoV-2 (also known as 2019-nCoV and Wuhan coronavirus).

In humans, coronaviruses cause respiratory infections, including the common cold, which are typically mild, though rarer forms such as SARS, MERS and SARS-CoV-2 (the cause of the 2019-20 COVID-19 outbreak) can be lethal. Symptoms vary in other species: in chickens, they cause an upper respiratory disease, while in cows and pigs coronaviruses cause diarrhea. There are no vaccines or antiviral drugs to prevent or treat human coronavirus infections. The coronaviruses HCoV-229E, -NL63, -OC43, and -HKU1 continually circulate in the human population and cause respiratory infections in adults and children worldwide In some embodiments, the compounds used herein are for treatment of alphacoronaviruses or betacoronaviruses. In some cases, the compounds used herein are for treatment of alphacoronaviruses. Non-limiting examples of alphacoronaviruses include HCoV-229E and HCoV-NL63. In some embodiments, the compounds used herein are for treatment of betacoronaviruses. Non-limiting examples of betacoronaviruses are HCoV-HKU1, HCoV-OC43, Middle East respiratory syndrome coronavirus (MERS-CoV), the severe acute respiratory syndrome coronavirus (SARS-CoV), and SARS-CoV-2. In some embodiments, the compounds used herein are for treatment of coronaviruses which are associated with SARS, MERS, and COVID-19. In some embodiments, coronaviruses are associated with SARS. In some embodiments, coronaviruses are associated with MERS. In some embodiments, coronaviruses are associated with COVID-19.

In some embodiments, the compounds disclosed herein can be used in the treatment of coronavirus, wherein the compound binds to free virus, or inhibits a coronavirus protease. In some cases, the compound can target both (free virus and protease).

In humans, common symptoms of coronavirus are fever, cough, shortness of breath, and myalgia.

Non-limiting examples of picornavirus infections include rhinovirus mediated conditions and rhinovirus infections. The terms "rhinovirus mediated condition" and "rhinovirus infection" as used herein, are used interchangeably to mean the disease caused by an infection with a rhinovirus.

Picornaviruses infect both humans and animals, can cause severe paralysis (paralytic poliomyelitis), aseptic meningitis, hepatitis, pleurodynia, myocarditis, skin rashes, and colds; although asymptomatic infection is common. Several medically important genera are members of this family, such as enterovirus (including poliovirus (PV), rhinoviruses, and human enteroviruses (e.g. coxsackie viruses)); hepatovirus which includes hepatitis A virus (HAV); and aphthoviruses which include the foot- and mouth disease virus (FMDV). Rhinoviruses are recognized as the principle cause of the common cold in humans, and comprise three different species: A, B, and C. Transmission is primarily by the aerosol route and the virus replicates in the nose.

In some embodiments, the compounds disclosed herein can be used in the treatment of picornavirus infection. In some embodiments, the compounds disclosed herein can be used in the treatment of rhinovirus infection. In some embodiments, the compounds disclosed herein can be used in the treatment of rhinovirus infection wherein the compound binds to free virus, or inhibits a rhinovirus protease. In some cases, the compound can target both (free virus and protease).

The terms, "disease", "disorder", and "condition" may be used interchangeably here to refer to norovirus or coronavirus virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the terms "inhibition of the replication of noroviruses" and "inhibition of the replication of coronaviruses" includes both the reduction in the amount of virus replication (e.g. the reduction by at least 10%) and the complete arrest of virus replication (i.e., 100% reduction in the amount of virus replication). In some embodiments, the replication of norovirus or coronavirus viruses are inhibited by at least 50%, at least 65%, at least 75%, at least 85%, at least 90%, or at least 95%.

Norovirus or coronavirus virus replication can be measured by any suitable method known in the art. For example, norovirus or coronavirus viral titer in a biological sample (e.g. an infected cell culture) or in humans (e.g. lung viral titer in a patient) can be measured. More specifically, for cell based assays, in each case cells are cultured in vitro, virus is added to the culture in the presence or absence of a test agent, and after a suitable length of time a virus-dependent endpoint is evaluated. Such assays are known in the art. A first type of cell assay that can be used in the disclosure depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed in the disclosure depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer (or titer)" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. To determine the titer, several dilutions will be prepared, such as $10^{-1}$, $10^{-2}$, $10^{-3}$, $10^{-8}$.

As used herein, the terms "treat", "treatment" and "treating" refer to both therapeutic and prophylactic treatments. For example, therapeutic treatments includes the reduction or mitigation of the progression, severity and/or duration of norovirus or coronavirus mediated conditions, or the amelioration of one or more symptoms (specifically, one or more discernible symptoms) of norovirus or coronavirus mediated conditions, resulting from the administration of one or more therapies (e.g., one or more therapeutic agents such as a compound or composition of the disclosure). In specific embodiments, the therapeutic treatment includes the amelioration of at least one measurable physical parameter of a norovirus or coronavirus mediated condition. In other embodiments the therapeutic treatment includes the inhibition of the progression of a norovirus or coronavirus mediated condition, either physically by, e.g., stabilization of a discernible symptom, physiologically by, e.g., stabilization of a physical parameter, or both. In other embodiments the therapeutic treatment includes the reduction or stabilization of norovirus or coronavirus mediated infections. Antiviral drugs can be used in the community setting to treat people who already have norovirus or coronavirus to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious norovirus or coronavirus complications live in close contact with each other (e.g. in a hospital ward, daycare center, prison, nursing home, etc.). It also includes the use among populations who require protection from the norovirus or coronavirus but who either do not get protection after vaccination (e.g. due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the norovirus or coronavirus or not considered at high risk for complications, in order to reduce the chances of getting infected with norovirus or coronavirus and passing it on to a high-risk person in close contact with him (for instance, healthcare workers, nursing home workers, etc.).

In some embodiments, the methods of the disclosure are a preventative or "prophylactic" measure to a patient, specifically a human, having a predisposition to complications resulting from infection by a norovirus or coronavirus virus. Prophylactic use includes use in situations in which an "index case" or an "outbreak" has been confirmed, in order to prevent the spread of infection in the rest of the community or population group.

In embodiments, the methods of the disclosure are applied as a "prophylactic" measure to members of a community or population group, specifically humans, in order to prevent the spread of infection.

As used herein, an "effective amount" refers to an amount sufficient to elicit the desired biological response. In the present disclosure the desired biological response is to inhibit the replication of norovirus or coronavirus, to reduce the amount of norovirus or coronavirus or to reduce or ameliorate the severity, duration, progression, or onset of a norovirus or coronavirus virus infection, prevent the advancement of a norovirus or coronavirus infection, prevent the recurrence, development, onset or progression of a symptom associated with a norovirus or coronavirus infection, or enhance or improve the prophylactic or therapeutic effect(s) of another therapy used against norovirus or coronavirus infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti-viral agents, e.g., when co-administered with an anti-norovirus or coronavirus medication, an “effective amount” of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, a safe and effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds for uses described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Combination Therapy

The compounds described herein can be used in combination therapy, i.e., in conjunction with other anti-norovirus or anti-coronavirus compounds, or in conjunction with a vaccine. Combination therapy can be particularly advantageous where a patient might be exposed to more than one form of the norovirus or coronavirus virus.

A safe and effective amount can be achieved in the method or pharmaceutical composition of the disclosure employing a compound disclosed herein, or a pharmaceutically acceptable salt thereof alone or in combination with an additional suitable therapeutic agent, for example, an antiviral agent or a vaccine. When “combination therapy” is employed, a safe and effective amount can be achieved using a first amount of a compound disclosed herein, or a pharmaceutically acceptable salt thereof, and a second amount of an additional suitable therapeutic agent (e.g. an antiviral agent or vaccine).

In embodiments, the compound disclosed herein, or a pharmaceutically acceptable salt, and the additional therapeutic agent, are each administered in a safe and effective amount (i.e., each in an amount which would be therapeutically effective if administered alone). In other embodiments, the compound disclosed herein, or a pharmaceutically acceptable salt thereof, and the additional therapeutic agent, are each administered in an amount which alone does not provide a therapeutic effect (a sub-therapeutic dose). In yet other embodiments, the compound disclosed herein, or a pharmaceutically acceptable salt thereof can be administered in a safe and effective amount, while the additional therapeutic agent is administered in a sub-therapeutic dose. In still other embodiments, the compound disclosed herein, a pharmaceutically acceptable salt thereof can be administered in a sub-therapeutic dose, while the additional therapeutic agent, for example, a suitable antiviral therapeutic agent is administered in a safe and effective amount.

As used herein, the terms “in combination” or “co-administration” can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

In embodiments, the present disclosure is directed to methods of combination therapy for inhibiting the virus's replication in biological samples or patients, or for treating or preventing norovirus or coronavirus infections in patients using the compounds or pharmaceutical compositions described herein, e.g., a compound disclosed herein, or a pharmaceutically acceptable salt thereof. Accordingly, pharmaceutical compositions also include those comprising a compound as disclosed herein (e.g., an inhibitor of virus replication) in combination with an anti-viral compound exhibiting anti-Norovirus or coronavirus virus activity.

Methods of use of the compounds and compositions disclosed herein also include combination of chemotherapy with a compound or composition disclosed herein, or a pharmaceutically acceptable salt thereof or with a combination of a compound or composition of this disclosure with another anti-viral agent.

When co-administration involves the separate administration of the first amount of a compound disclosed herein, or a pharmaceutically acceptable salt thereof and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound disclosed herein, or a pharmaceutically acceptable salt thereof and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the disclosure) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-viral agent) to a subject.

It is understood that the method of co-administration of a first amount of a compound disclosed herein, or a pharmaceutically acceptable salt thereof and a second amount of an additional therapeutic agent can result in an enhanced or synergistic therapeutic effect, wherein the combined effect is greater than the additive effect that would result from separate administration of the first amount of the compound disclosed herein, or a pharmaceutically acceptable salt thereof and the second amount of the additional therapeutic agent.

As used herein, the term "synergistic" refers to a combination of a compound disclosed herein and another therapy (e.g., a prophylactic or therapeutic agent), which is more effective than presumed additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using compounds as disclosed herein is in combination with a virus vaccine, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Chiral Separations

The compounds described herein can have asymmetric centers and occur as racemates, racemic mixtures, individual diastereomers or enantiomers, with all isomeric forms being included in the present disclosure. Compounds of the present disclosure having a chiral center can exist in and be isolated in optically active and racemic forms. Some compounds can exhibit polymorphism. The present disclosure encompasses racemic, optically-active, polymorphic, or stereoisomeric forms, or mixtures thereof, of a compound of the disclosure, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

The present disclosure will be better understood with reference to the following non-limiting examples.

Testing of Activity of Compounds

In Vitro Antiviral Assays

Norovirus antiviral assays:

Cell-based antiviral assays: The antiviral effects of inhibitors disclosed herein are examined in the Norwalk virus replicon harboring cells (HG23 cells). Briefly, confluent and semi-confluent cells are incubated with medium containing DMSO (<0.1%) or each compound (up to 100 μM) for 48 h. After the incubation, total RNA was extracted and viral genome is quantitated with real-time quantitative RT-PCR (qRT-PCR). The $EC_{50}$ values are determined by GraphPad-Prism software. In addition to Norwalk virus replicon, the CPE (cytopathic effect) antiviral activities of the inhibitors are determined using FCoV (feline coronavirus), MERS-CoV (Middle East respiratory syndrome-related coronavirus), SARS-CoV (severe acute respiratory syndrome-related coronavirus), human coronavirus 229E, murine norovirus, and human rhinovirus.

Viral protease assays: The antiviral activities of inhibitors disclosed herein are determined by FRET (Fluorescence Resonance Energy Transfer) assay. Purified viral protease is incubated with the protease substrate peptide (Edans-DFHLQ/GP-Dabcyl) and inhibitor, and $IC_{50}$ values are subsequently determined by the fluorescence signals.

All references provided herein are incorporated herein in its entirety by reference. As used herein, all abbreviations, symbols and conventions are consistent with those used in the contemporary scientific literature. See, e.g., Janet S. Dodd, ed., The ACS Style Guide: A Manual for Authors and Editors, 2nd Ed., Washington, D.C.: American Chemical Society, 1997.

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A compound as recited in Table A, or a pharmaceutically acceptable salt thereof:

TABLE A

| Compound no. | Structure |
|---|---|
| A1 | 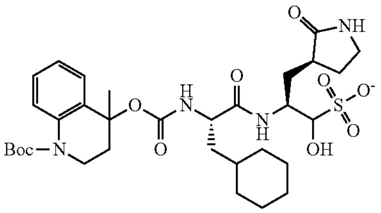 [SMILES: CC(C)(C)OC(=O)N1CCC(C)(OC(=O)N[C@@H](CC2CCCCC2)C(=O)N[C@@H](C[C@@H]2CCNC2=O)C(O)S(=O)(=O)[O-])c2ccccc21] |
| A2 | 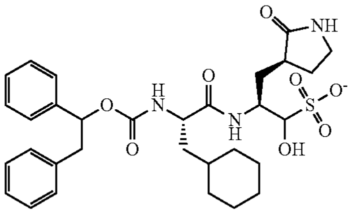 [SMILES: O=C(N[C@@H](CC1CCCCC1)C(=O)N[C@@H](C[C@@H]1CCNC1=O)C(O)S(=O)(=O)[O-])OC(Cc1ccccc1)c1ccccc1] |
| A3 | 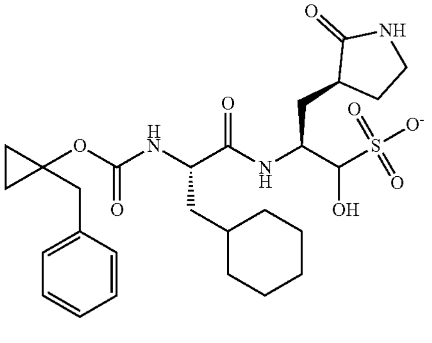 [SMILES: O=C(N[C@@H](CC1CCCCC1)C(=O)N[C@@H](C[C@@H]1CCNC1=O)C(O)S(=O)(=O)[O-])OC1(Cc2ccccc2)CC1] |
| A4 | 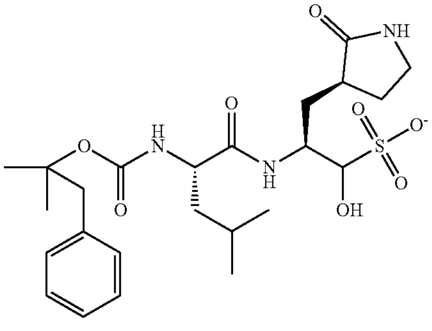 [SMILES: CC(C)C[C@H](NC(=O)OC(C)(C)Cc1ccccc1)C(=O)N[C@@H](C[C@@H]1CCNC1=O)C(O)S(=O)(=O)[O-]] |

TABLE A-continued
| Compound no. | Structure |
|---|---|
| A5 | 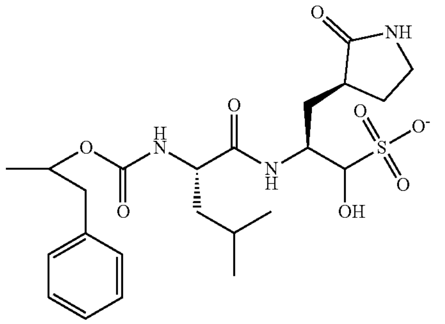 [SMILES: CC(C)C[C@H](NC(=O)OC(C)Cc1ccccc1)C(=O)N[C@@H](C[C@@H]1CCNC1=O)C(O)S(=O)(=O)[O-]] |
| A6 | 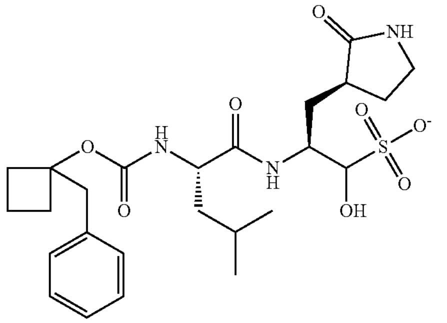 [SMILES: CC(C)C[C@H](NC(=O)OC1(Cc2ccccc2)CCC1)C(=O)N[C@@H](C[C@@H]1CCNC1=O)C(O)S(=O)(=O)[O-]] |
| A7 | 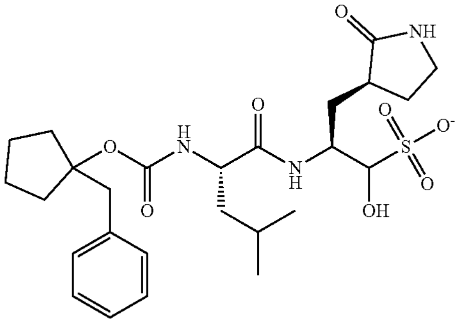 [SMILES: CC(C)C[C@H](NC(=O)OC1(Cc2ccccc2)CCCC1)C(=O)N[C@@H](C[C@@H]1CCNC1=O)C(O)S(=O)(=O)[O-]] |
| A8 | 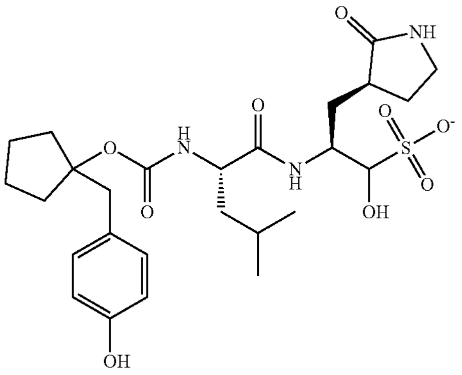 [SMILES: CC(C)C[C@H](NC(=O)OC1(Cc2ccc(O)cc2)CCCC1)C(=O)N[C@@H](C[C@@H]1CCNC1=O)C(O)S(=O)(=O)[O-]] |
TABLE A-continued
| Compound no. | Structure |
|---|---|
| A9 | 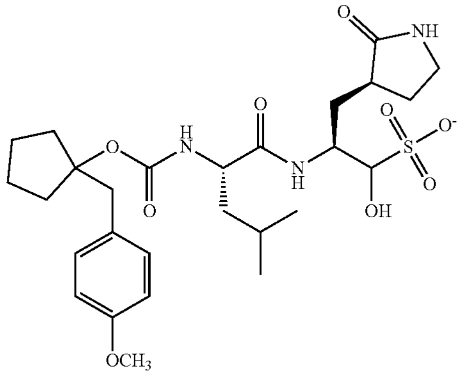 [SMILES: COc1ccc(CC2(OC(=O)N[C@@H](CC(C)C)C(=O)N[C@@H](C[C@@H]3CCNC3=O)C(O)S(=O)(=O)[O-])CCCC2)cc1] |
| A10 | 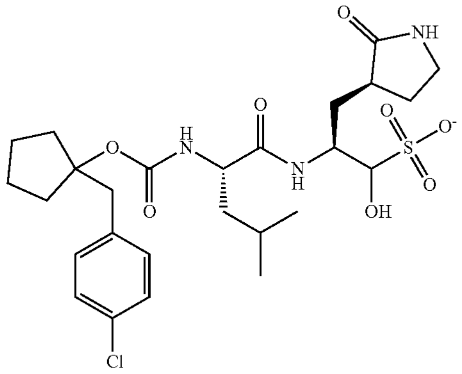 [SMILES: CC(C)C[C@H](NC(=O)OC1(Cc2ccc(Cl)cc2)CCCC1)C(=O)N[C@@H](C[C@@H]1CCNC1=O)C(O)S(=O)(=O)[O-]] |
| A11 | 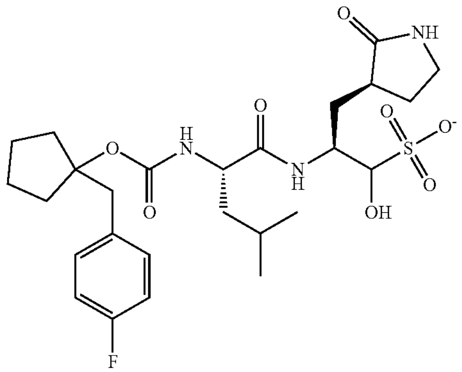 [SMILES: CC(C)C[C@H](NC(=O)OC1(Cc2ccc(F)cc2)CCCC1)C(=O)N[C@@H](C[C@@H]1CCNC1=O)C(O)S(=O)(=O)[O-]] |
| A12 | 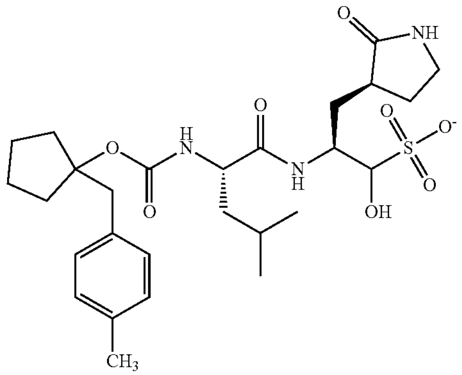 |

TABLE A-continued
| Compound no. | Structure |
| --- | --- |
| A13 | 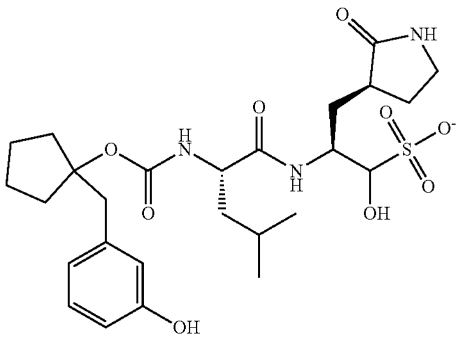 [SMILES: CC(C)C[C@H](NC(=O)OC1(Cc2cccc(O)c2)CCCC1)C(=O)N[C@@H](C[C@@H]1CCNC1=O)C(O)S(=O)(=O)[O-]] |
| A14 | 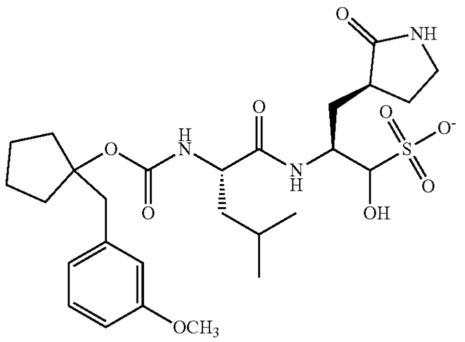 [SMILES: COc1cccc(CC2(OC(=O)N[C@@H](CC(C)C)C(=O)N[C@@H](C[C@@H]3CCNC3=O)C(O)S(=O)(=O)[O-])CCCC2)c1] |
| A15 | 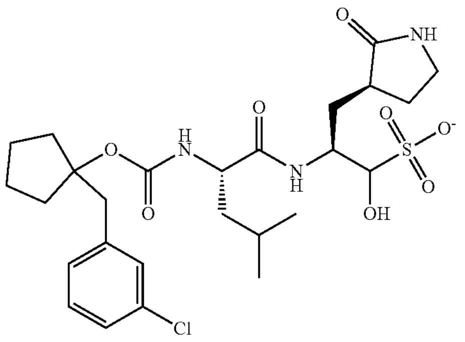 |
| A16 | 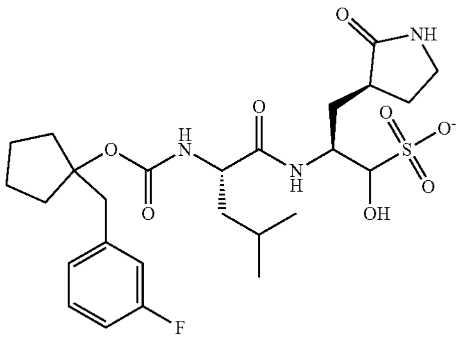 [SMILES: CC(C)C[C@H](NC(=O)OC1(Cc2cccc(Cl)c2)CCCC1)C(=O)N[C@@H](C[C@@H]1CCNC1=O)C(O)S(=O)(=O)[O-]] |
| A17 | 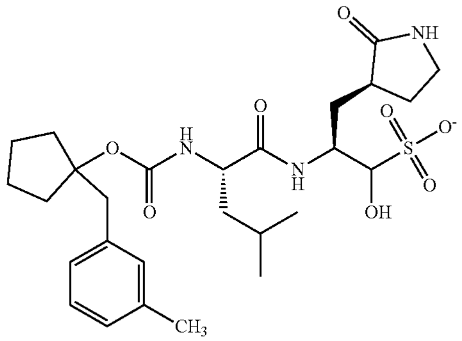 [SMILES: Cc1cccc(CC2(OC(=O)N[C@@H](CC(C)C)C(=O)N[C@@H](C[C@@H]3CCNC3=O)C(O)S(=O)(=O)[O-])CCCC2)c1] |
| A18 | 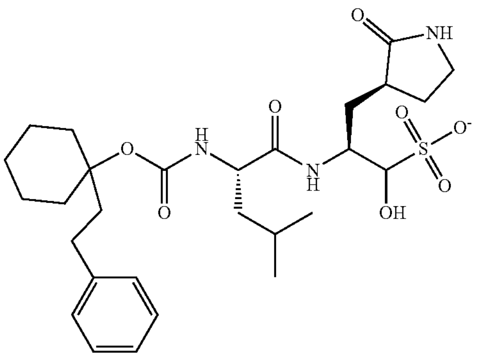 [SMILES: CC(C)C[C@H](NC(=O)OC1(CCc2ccccc2)CCCCC1)C(=O)N[C@@H](C[C@@H]1CCNC1=O)C(O)S(=O)(=O)[O-]] |
| A19 | 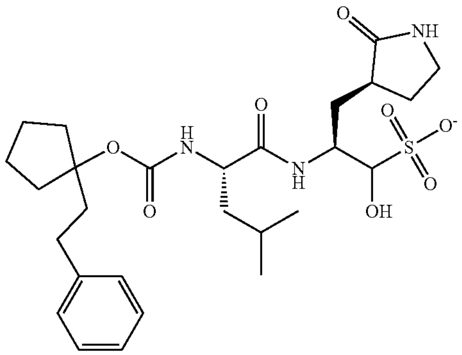 [SMILES: CC(C)C[C@H](NC(=O)OC1(CCc2ccccc2)CCCC1)C(=O)N[C@@H](C[C@@H]1CCNC1=O)C(O)S(=O)(=O)[O-]] |
| A20 | 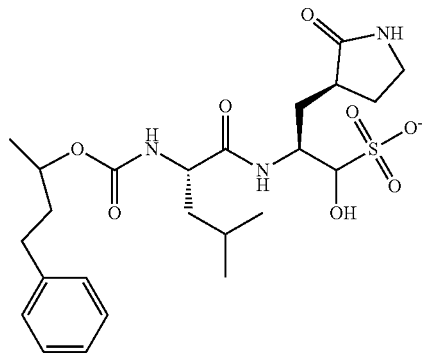 [SMILES: CC(C)C[C@H](NC(=O)OC(C)CCc1ccccc1)C(=O)N[C@@H](C[C@@H]1CCNC1=O)C(O)S(=O)(=O)[O-]] |

TABLE A-continued
| Compound no. | Structure |
|---|---|
| A21 | 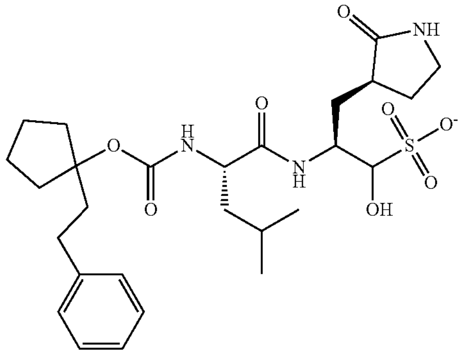 [SMILES: CC(C)C[C@H](NC(=O)OC1(CCc2ccccc2)CCCC1)C(=O)N[C@@H](C[C@@H]1CCNC1=O)C(O)S(=O)(=O)[O-]] |
| A22 | 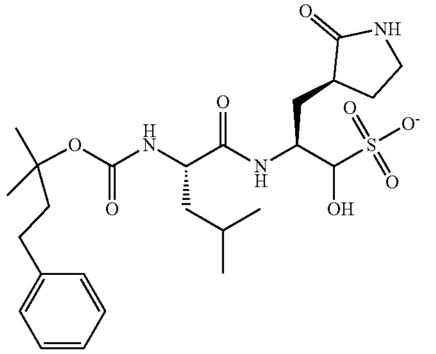 [SMILES: CC(C)C[C@H](NC(=O)OC(C)(C)CCc1ccccc1)C(=O)N[C@@H](C[C@@H]1CCNC1=O)C(O)S(=O)(=O)[O-]] |
| A23 | 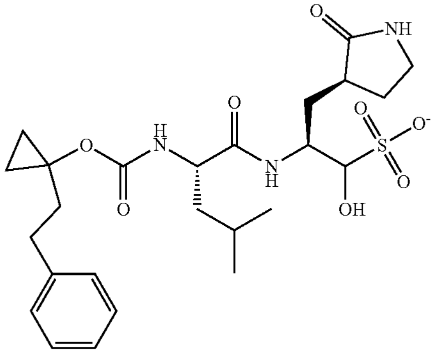 [SMILES: CC(C)C[C@H](NC(=O)OC1(CCc2ccccc2)CC1)C(=O)N[C@@H](C[C@@H]1CCNC1=O)C(O)S(=O)(=O)[O-]] |
| A24 | 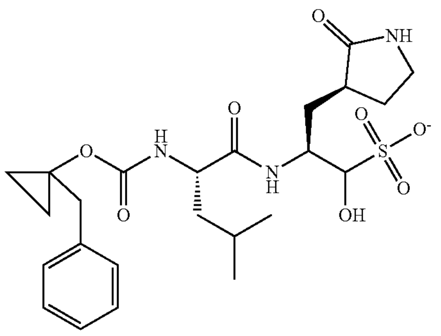 [SMILES: CC(C)C[C@H](NC(=O)OC1(Cc2ccccc2)CC1)C(=O)N[C@@H](C[C@@H]1CCNC1=O)C(O)S(=O)(=O)[O-]] |
TABLE A-continued
| Compound no. | Structure |
|---|---|
| A25 | 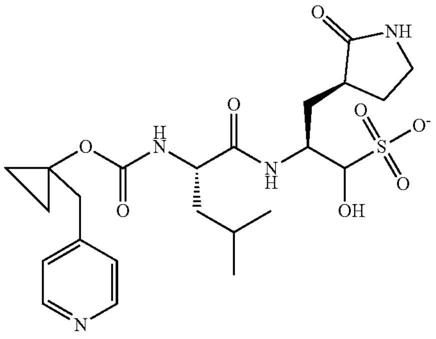 [SMILES: CC(C)C[C@H](NC(=O)OC1(Cc2ccncc2)CC1)C(=O)N[C@@H](C[C@@H]1CCNC1=O)C(O)S(=O)(=O)[O-]] |
| A26 | 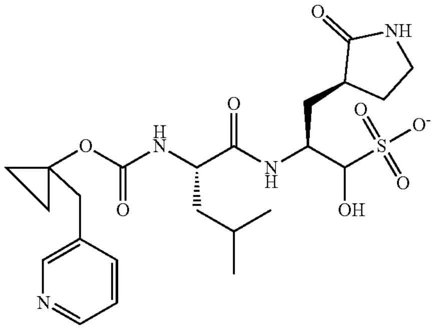 [SMILES: CC(C)C[C@H](NC(=O)OC1(Cc2cccnc2)CC1)C(=O)N[C@@H](C[C@@H]1CCNC1=O)C(O)S(=O)(=O)[O-]] |
| A27 | 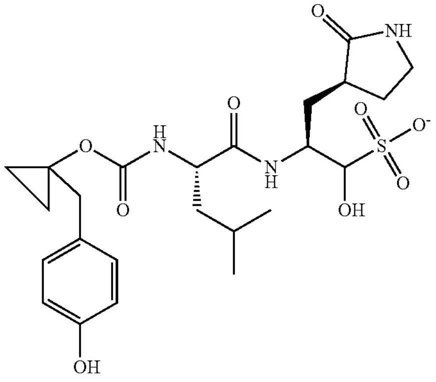 [SMILES: CC(C)C[C@H](NC(=O)OC1(Cc2ccc(O)cc2)CC1)C(=O)N[C@@H](C[C@@H]1CCNC1=O)C(O)S(=O)(=O)[O-]] |
| A28 | 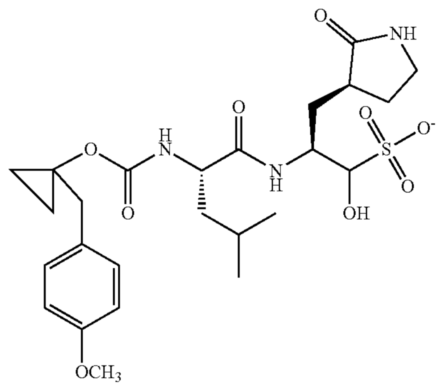 [SMILES: COc1ccc(CC2(OC(=O)N[C@@H](CC(C)C)C(=O)N[C@@H](C[C@@H]3CCNC3=O)C(O)S(=O)(=O)[O-])CC2)cc1] |

TABLE A-continued
| Compound no. | Structure |
|---|---|
| A29 | 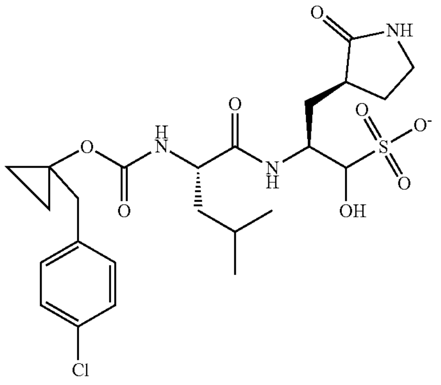 [SMILES: CC(C)C[C@H](NC(=O)OC1(Cc2ccc(Cl)cc2)CC1)C(=O)N[C@@H](C[C@@H]1CCNC1=O)C(O)S(=O)(=O)[O-]] |
| A30 | 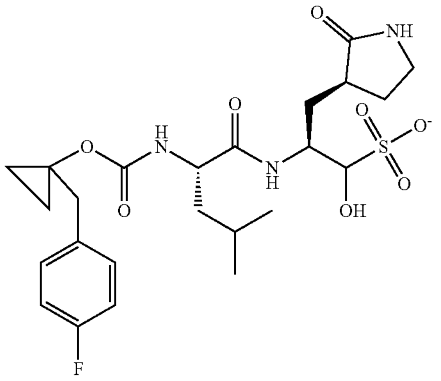 [SMILES: CC(C)C[C@H](NC(=O)OC1(Cc2ccc(F)cc2)CC1)C(=O)N[C@@H](C[C@@H]1CCNC1=O)C(O)S(=O)(=O)[O-]] |
| A31 | 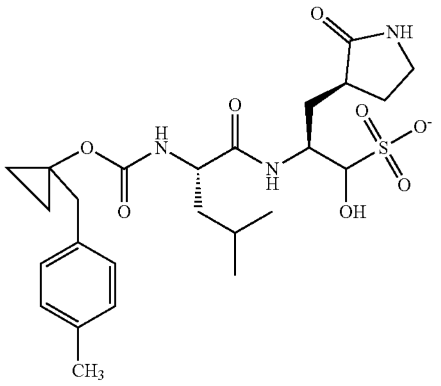 [SMILES: Cc1ccc(CC2(OC(=O)N[C@@H](CC(C)C)C(=O)N[C@@H](C[C@@H]3CCNC3=O)C(O)S(=O)(=O)[O-])CC2)cc1] |
| A32 | 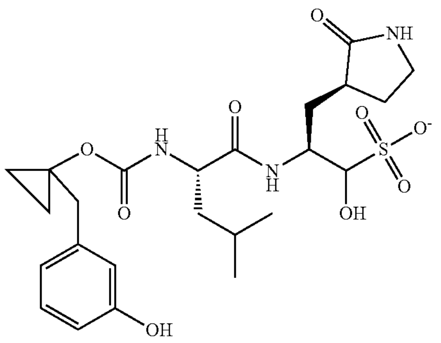 [SMILES: CC(C)C[C@H](NC(=O)OC1(Cc2cccc(O)c2)CC1)C(=O)N[C@@H](C[C@@H]1CCNC1=O)C(O)S(=O)(=O)[O-]] |
| A33 | 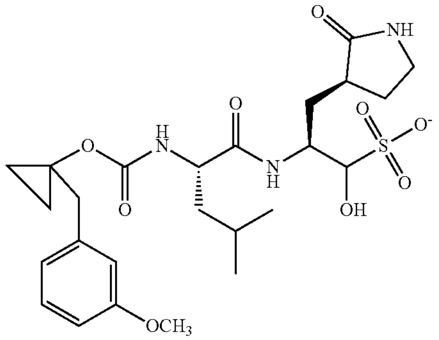 [SMILES: COc1cccc(CC2(OC(=O)N[C@@H](CC(C)C)C(=O)N[C@@H](C[C@@H]3CCNC3=O)C(O)S(=O)(=O)[O-])CC2)c1] |
| A34 | 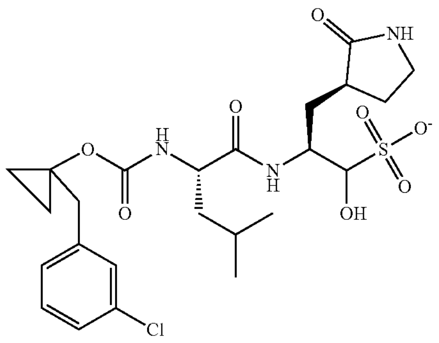 [SMILES: CC(C)C[C@H](NC(=O)OC1(Cc2cccc(Cl)c2)CC1)C(=O)N[C@@H](C[C@@H]1CCNC1=O)C(O)S(=O)(=O)[O-]] |
| A35 | 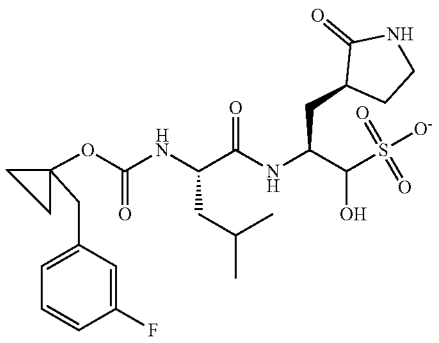 |
| A36 | 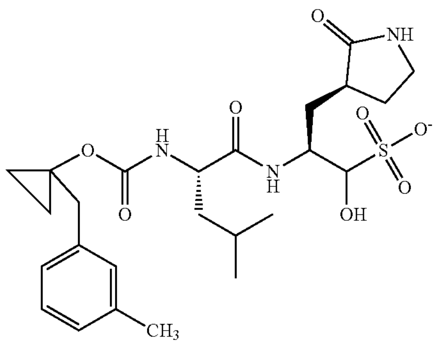 [SMILES: Cc1cccc(CC2(OC(=O)N[C@@H](CC(C)C)C(=O)N[C@@H](C[C@@H]3CCNC3=O)C(O)S(=O)(=O)[O-])CC2)c1] |

TABLE A-continued
| Compound no. | Structure |
|---|---|
| A37 | 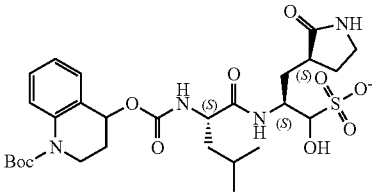 |
| A38 | 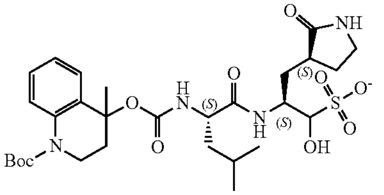 |
| A39 | 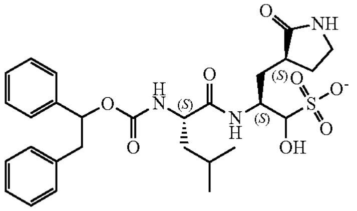 |
| A40 | 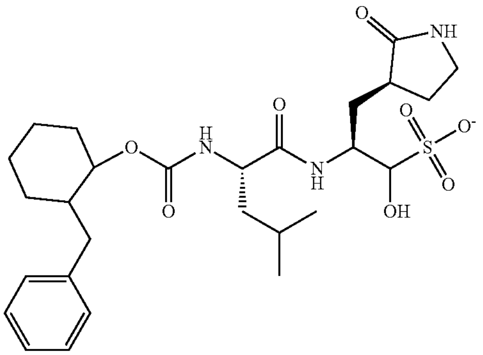 [SMILES: CC(C)C[C@H](NC(=O)OC1CCCCC1Cc1ccccc1)C(=O)N[C@@H](C[C@@H]1CCNC1=O)C(O)S(=O)(=O)[O-]] |
| A41 | 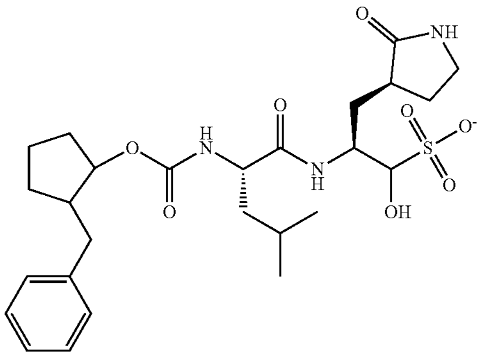 [SMILES: CC(C)C[C@H](NC(=O)OC1CCCC1Cc1ccccc1)C(=O)N[C@@H](C[C@@H]1CCNC1=O)C(O)S(=O)(=O)[O-]] |
| A42 | 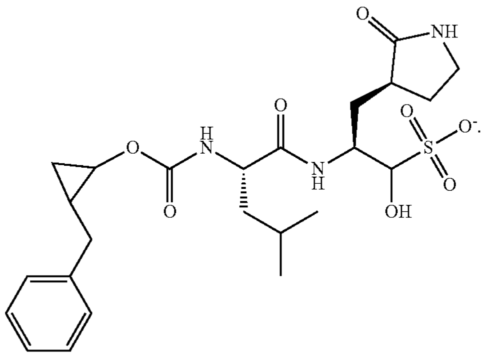 |
2. A pharmaceutical formulation comprising the compound or salt of claim 1 and a pharmaceutically acceptable excipient.
* * * * *